United States Patent
Zhang et al.

(10) Patent No.: US 8,629,164 B2
(45) Date of Patent: Jan. 14, 2014

(54) INHIBITORS OF NF-κB

(75) Inventors: Jie Zhang, Baltimore, MD (US); Drago Robert Sliskovic, Chelsea, MI (US); Charles E. Ducker, York, PA (US)

(73) Assignee: Profectus Biosciences, Inc., Baltimore, MD (US)

( * ) Notice: Subject to any disclaimer, the term of this patent is extended or adjusted under 35 U.S.C. 154(b) by 0 days.

(21) Appl. No.: 13/258,512

(22) PCT Filed: Mar. 25, 2010

(86) PCT No.: PCT/US2010/028610
§ 371 (c)(1),
(2), (4) Date: Sep. 22, 2011

(87) PCT Pub. No.: WO2010/111460
PCT Pub. Date: Sep. 30, 2010

(65) Prior Publication Data
US 2012/0015952 A1 Jan. 19, 2012

Related U.S. Application Data

(60) Provisional application No. 61/164,256, filed on Mar. 27, 2009, provisional application No. 61/255,096, filed on Oct. 27, 2009, provisional application No. 61/265,026, filed on Nov. 30, 2009.

(51) Int. Cl.
*A01N 43/40* (2006.01)
*A61K 31/44* (2006.01)
*C07D 213/22* (2006.01)

(52) U.S. Cl.
USPC ............................ 514/332; 546/255; 546/257

(58) Field of Classification Search
USPC ................................... 546/255, 257; 514/332
See application file for complete search history.

(56) References Cited

U.S. PATENT DOCUMENTS 6,566,394 B1 5/2003 Takeuchi

FOREIGN PATENT DOCUMENTS

| EP | 1219596 | 7/2002 |
|----|---------|--------|
| EP | 1541139 | 6/2005 |
| EP | 1600445 | 11/2005 |
| JP | 2008/259494 | 10/2008 |
| WO | WO-2010/127058 | 11/2010 |
| WO | WO-2010/148042 | 12/2010 |

OTHER PUBLICATIONS

Pinedo et al (2000) McMahon (2000).*
Aggarwal, "Inflammation and cancer: how hot is the link?", Biochemical Pharmacology, 72(11): 1605-1621 (Nov. 30, 2006; e-publication: Aug. 4, 2006).
Arcaroli, "Variant IRAK-1 haplotype is associated with increased nuclear factor-κB activation and worse outcomes in sepsis", American Journal of Respiratory and Critical Care Medicine, 173(12): 1335-1341 (Mar. 30, 2006).
Argyropoulos, "Immunosuppressive drugs in HIV disease", Current Topics in Medicinal Chemistry, 6(16): 1769-1789 (2006).
Ariga, "Inhibition of tumor necrosis factor α-induced nuclear translocation and activation of NF-κB by dehydroxymethylepoxyquinomicin", Journal of Biological Chemistry, 277(27): 24625-24630 (Jul. 5, 2002).
Atreya, "NF-κB in inflammatory bowel disease", Journal of Internal Medicine, 263(6): 591-596 (Jun. 2008).
Baba, "Recent status of HIV-1 gene expression inhibitors", Antiviral Research, 71(2-3): 301-306 (Sep. 2006; e-publication Feb. 3, 2006).
Barbie, "Systematic RNA interference reveals that oncogenic *KRAS*-driven cancers require TBK1", Nature 462(7269): 108-112 (Nov. 5, 2009).
Barnes, "Nuclear factor-κB", Int J Biochem Cell Biol 29(6): 867-870 (Jan. 1997).
Bosisio, "A hyper-dynamic equilibrium between promoter-bound and nucleoplasmic dimers controls NF-κB-dependent gene activity", Embo Journal, 25(4): 798-810 (2006; e-publication Feb. 9, 2006).
Bouma, "The immunological and genetic basis of inflammatory bowel disease", Nature Reviews Immunology, 3(7): 521-533 (Jul. 2003).
Burstein, "Dying for NF-κB? Control of cell death by transcriptional regulation of the apoptotic machinery", Current Opinions in Cell Biology, 15(6): 732-737 (Dec. 2003).
Calzado, "NF-κB inhibitors for the treatment of inflammatory diseases and cancer", Current Medicinal Chemistry, 14(3): 367-376 (2007).

(Continued)

*Primary Examiner* — Paul V. Ward
(74) *Attorney, Agent, or Firm* — Howson & Howson LLP; Alan M. Godon, Esq.

(57) ABSTRACT

The invention relates to compounds of formulae (1) and (2):

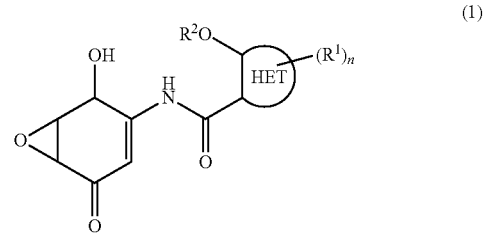

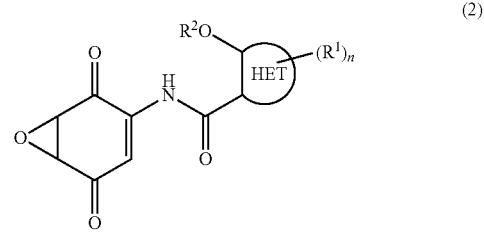

and pharmaceutically acceptable salts thereof for the treatment of cancer, inflammation, auto-immune diseases, diabetes and diabetic complications, infection, cardiovascular disease and ischemia-reperfusion injuries.

9 Claims, 11 Drawing Sheets

(56) References Cited

OTHER PUBLICATIONS

Chaicharoenpong, "Synthesis and structure-activity relationship of dehydroxymethylepoxyquinomicin analogues as inhibitors of NF-κB functions", Bioorganic and Medicinal Chemistry, 10(12): 3933-3939 (Dec. 2002).
Cheng, "Relationship between the inhibition constant ($K_i$) and the concentration of inhibitor which causes 50 per cent inhibition ($I_{50}$) of an enzymatic reaction", Biochemical Pharmacology, 22:3099-3108 (Dec. 1, 1973).
Dejardin, "The alternative NF-κB pathway from biochemistry to biology: pitfalls and promises for future drug development", Biochemical Pharmacology, 72:1161-1179 (Oct. 30, 2006; e-publication: Sep. 12, 2006).
Flory, "Influenza virus-induced NF-κB-dependent gene expression is mediated by overexpression of viral proteins and involves oxidative radicals and activation of IκB kinase", Journal of Biological Chemistry, 275(12): 8307-8314 (Mar. 24, 2000).
Giri, "Mechanism of amyloid peptide induced CCR5 expression in monocytes and its inhibition by siRNA for Egr-1", Am J Physiol Cell Physiol 289(2): C264-276 (Mar. 2, 2005).
Goldring, "Formation of a synovial-like membrane at the bone-cement interface. Its role in bone resorption and implant loosening after total hip replacement", Arthritis and Rheumatism 29(7): 836-842 (Jul. 1986).
Greten, "The IKK/NF-κB activation pathway—a target for prevention and treatment of cancer", Cancer Letters, 206(2): 193-199 (Apr. 8, 2004).
Gregersen, "REL, encoding a member of the NF-κB family of transcription factors, is a newly defined risk locus for rheumatoid arthritis", Nature Genetics, 41(7): 820-823 (Jul. 2009; e-publication: Jun. 7, 2009).
Häcker, "Regulation and function of IKK and IKK-related kinases", Sciences STKE 2006(357): 1-19 (Oct. 17, 2006).
Harris, "The problem is osteolysis", Clinical Orthopaedics and Related Research, 311: 46-53 (Feb. 1995).
Hayden, "Signaling to NF-κB", Genes and Development, 18(18): 2195-2224 (Sep. 15, 2004).
Hayden, "NF-κB and the immune response", Oncogene 25(51): 6758-6780 (Dec. 15, 2006a).
Hayden, "SnapShot: NF-κB Signaling Pathways", Cell, 127(6): 1286-1287 (Dec. 15, 2006).
Helbig, "NF-κB promotes breast cancer cell migration and metastasis by inducing the expression of the chemokine receptor CXCR4", Journal of Biological Chemistry, 278(24):21631-21638 (Jun. 13, 2003).
Iordanskiy, "B-oligomer of pertussis toxin inhibits HIV-1 LTR-driven transcription through suppression of NF-κB p65 subunit activity", Virology 302(1):195-206 (Oct. 10, 2002).
Israël, "The IKK complex: an integrator of all signals that activate NF-κB?", Trends in Cell Biology, 10(4): 129-133 (Apr. 2000).
Jung, "Correction of radiation sensitivity in ataxia telangiectasia cells by a truncated IκB-α", Science, 268(5217): 1619-1621 (Jun. 16, 1995).
Karin, "How NF-κB is activated: the role of the IκB kinase (IKK) complex", Oncogene, 18(49): 6867-6874 (Nov. 22, 1999).
Karin, "Nuclear factor-κB in cancer development and progression", Nature 441(7092): 431-436 (May 25, 2006).
Ketas, "Cell surface expression of CCR5 and other host factors influence the inhibition of HIV-1 infection of human lymphocytes by CCR5 ligands", Virology, 364(2):281-90 (Aug. 1, 2007; e-publication: Apr. 10, 2007).
Lawrence, "Estimates of the prevalence of arthritis and selected musculoskeletal disorders in the United States", Arthritis and Rheumatism, 41(5): 778-799 (May 1998).
Liao, "Genetic evidence for a common pathway mediating oxidative stress, inflammatory gene induction, and aortic fatty streak formation in mice", J Clin Invest, 94(2): 877-884 (Aug. 1994).
Liu, "Functional analysis of the proximal CCR5 promoter", AIDS Research and Human Retroviruses, 14(17): 1509-1519 (Nov. 20, 1998).
Maruyama, "Thrombin activates NF-κB through thrombin receptor and results in proliferation of vascular smooth muscle cells: role of thrombin in atherosclerosis and restenosis", Annals of the NY Academy of Sciences, 811: 429-436 (Apr. 15, 1997).
Meylan, "Requirement for NF-κB signaling in a mouse model of lung adenocarcinoma", Nature, 462(7269):104-107 (Nov. 5, 2009).
Mukerjee, "Association of p65 and C/EBPβ with HIV-1 LTR modulates transcription of the viral promoter", Journal of Cellular Biochemistry, 100(5):1210-6 (Apr. 1, 2006).
Natoli, "Interactions of NF-κB with chromatin: the art of being at the right place at the right time", Nature Immunology, 6(5): 439-445 (May 2005).
Neurath, "Cytokine gene transcription by NF-kappa B family members in patients with inflammatory bowel disease", Annals of the NY Academy of Sciences, 859: 149-159 (Nov. 17, 1998).
Niu, "Protection against lipopolysaccharide-induced myocardial dysfunction in mice by cardiac-specific expression of soluble Fas", J Mol Cell Cardiol 44(1): 160-169 (Jan. 2008; e-publication: Oct. 4, 2007).
Pahl, "Expression of influenza virus hemagglutinin activates transcription factor NF-κB", Journal of Virology 69(3): 1480-1484 (Mar. 1995).
Palmieri, "Inhibition of HIV-1 replication in primary human monocytes by the IκB-αS32/36A repressor of NF-κb", Retrovirology 1(1): 45 (Dec. 21, 2004).
Pihlstrom, Periodontal diseases, Lancet, 366(9499): 1809-1820 (Nov. 19, 2005).
Platt, "Effects of CCR5 and CD4 cell surface concentrations on infections by macrophagetropic isolates of human immunodeficiency virus type 1", Journal of Virology, 72(4): 2855-2864 (Apr. 1998).
Reeves, "Sensitivity of HIV-1 to entry inhibitors correlates with envelope/coreceptor affinity, receptor density, and fusion kinectics", Proceedings National Academy Sciences USA, 99(25): 16249-16254 (Dec. 10, 2002; e-publication: Nov. 20, 2002).
Rizzi, "Inhibition of intra- and extra-cellular Tat function and HIV expression by pertussis toxin B-oligomer", European Journal of Immunology, 34(2): 530-536 (Feb. 2004).
Saccani, "Degradation of promoter-bound p65/RelA is essential for the prompt termination of the nuclear factor κB response", J Exp Med 200(1): 107-113 (Jul. 5, 2004; e-publication: Jun. 28, 2004).
Scheidereit, "IκB kinase complexes: gateways to NF-κB activation and transcription", Oncogene, 25(51): 6685-6705 (Oct. 30, 2006).
Sui, "Human immunodeficiency virus-encoded Tat activates glycogen synthase kinase-3β to antagonize nuclear factor-κB survival pathway in neurons", European Journal of Neuroscience, 23(10): 2623-2634 (May 2006).
Tergaonkar, "NF B pathway: a good signaling paradigm and therapeutic target", International Journal of Biochemistry and Cell Biology, 38(10): 1647-1653 (2006).
Tilg, "Gut, inflammation and osteoporosis: basic and clinical concepts", Gut, 57(5): 684-694 (May 2008).
Suzuki, "Preparation and biological activities of optically active dehydroxymethylepoxyquinomicin, a novel NF-κB inhibitor", Tetrahedron, 60:7061-7066 (Aug. 2004).
Umezawa, "Inhibition of tumor growth by NF-κB inhibitors", Cancer Sci, 97(10):990-995 (Oct. 2006; e-publication: Aug. 22, 2006).
Williams, "NF-κB p50 promotes HIV latency through HDAC recruitment and repression of transcriptional initiation", Embo Journal, 25(1): 139-149 (Jan. 11, 2006; e-publication: Dec. 1, 2005).
Williams, "Sustained Induction of NF-κB Is Required for Efficient Expression of Latent HIV-1", Journal of Virology 81(11):6043-56 (Jun. 2007; e-publication: Mar. 21, 2007).
Wirtz, "Mouse models of inflammatory bowel disease", Advanced Drug Delivery Reviews, 59(11): 1073-1083 (Sep. 30, 2007; e-publication: Aug. 16, 2007).
Yamamoto, "Inactivation of NF-κB components by covalent binding of (−)-dehydroxymethylepoxyquinomicin to specific cysteine residues", Journal of Medicinal Chemistry, 51(8):5780-5788 (Sep. 25, 2008; e-publication: Aug. 26, 2008).

(56) References Cited

OTHER PUBLICATIONS

Watanabe, "Hematopoietic stem cell-engrafted NOD/SCID/IL2Rγ$^{null}$ mice develop human lymphoid systems and induce long-lasting HIV-1 infection with specific humoral immune responses", Blood, 109(11):212 (Jan. 2007; e-publication: Sep. 5, 2006).

International Search Report dated Jul. 28, 2010 and issued in International Patent Application No. PCT/US2010/028610.

International Search Report dated Jul. 16, 2010 and issued in International Patent Application No. PCT/US2010/032880.

International Search Report dated Sep. 23, 2010 and issued in International Patent Application No. PCT/US2010/038774.

English translation of Japanese Patent Publication No. 2008259494.

Kalergis, "Modulation of nuclear factor-κB activity can influence the susceptibility to systemic lupus erythematosus", Immunology, 128:e306-E314 (2009; e-publication: Nov. 7, 2008).

Kurylowicz, "The role of nuclear factor-κB in the development of autoimmune diseases: a link between genes and environment", Acta Biochimica Polonica, 55(4): 629-647 (2008; e-publication: Dec. 16, 2008).

English translation of an Office Action dated Jul. 12, 2013 and issued in corresponding Chinese Patent Application No. 201080020009.9

\* cited by examiner

| compound | target | species | n | concentration | inhibition (%) |
|---|---|---|---|---|---|
| Example 2 | CYP450, 1A2 | human | 2 | 10 uM | 15 |
| Example 2 | CYP450, 2C19 | human | 2 | 10 uM | 9 |
| Example 2 | CYP450, 2C9 | human | 2 | 10 uM | 6 |
| Example 2 | CYP450, 2D6 | human | 2 | 10 uM | 12 |
| Example 2 | CYP450, 3A4 | human | 2 | 10 uM | -5 |
| Example 2 | hERG K-channel | human | 2 | 10 uM | 0 |

INHIBITORS OF NF-κB

CROSS REFERENCE TO RELATED APPLICATIONS

This application is a US national phase of International Patent Application No. PCT/US2010/028610, filed Mar. 25, 2010, which claims the benefit of the priorities of U.S. Provisional Patent Application No. 61/164,256, filed Mar. 27, 2009; U.S. Provisional Patent Application No. 61/255,096, filed Oct. 27, 2009; and U.S. Provisional Patent Application No. 61/265,026, filed Nov. 30, 2009. These priority applications are herein incorporated by reference.

FIELD OF INVENTION

The invention relates to compounds of formulae (1) and (2),

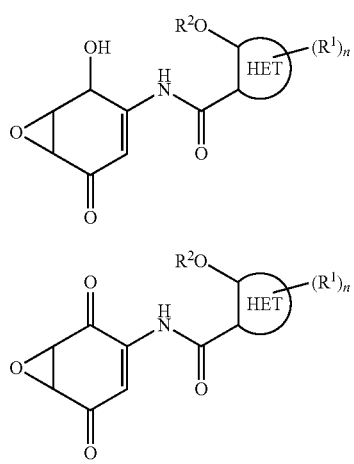

and pharmaceutically acceptable salts thereof for the treatment of cancer, inflammation, auto-immune diseases, diabetes and diabetic complications, infection, cardiovascular disease and ischemia-reperfusion injuries.

BACKGROUND OF INVENTION

NF-κB (nuclear factor κ-light-chain-enhancer of activated B cells) is a family of transcription factors that consists of hetero- or homo-dimers of p65 (RelA), c-Rel, RelB, p50 (NF-κB1), and p52 (NF-κB$_2$) (Dejardin 2006). In the classical, or canonical pathway of NF-κB, stimulation of a variety of cell membrane receptors leads to phosphorylation, ubiquitination, and proteasomal degradation of the IκBs (inhibitor proteins), which results in the nuclear translocation of the p65/50 hetero-dimer that turns on transcription. The canonical path can be effectively blocked by inhibition of IκBβ kinase, 26S proteasome, or p65 binding to DNA. The alternative, or non-canonical path, is regulated through proteolysis of the inhibitory ankyrin containing protein NF-κB2/p100 to release p52, which typically dimerizes with RelB. In addition, there is a "hybrid" path that activates p52/c-Rel and p52/p65. The non-canonical or "hybrid" paths are not susceptible to IκBβ kinase or proteasomal inhibitors. These paths are most effectively inhibited by antagonizing RelB or c-Rel binding to DNA. The canonical and non-canonical paths are associated with different aspects of specific diseases through activations of distinctive groups of genes. Thus, selective inhibition of either the canonical, or noncanonical pathway, or both, under different disease states, is believed to be a most effective approach to ameliorate the underlining disease conditions.

NF-κB activation has been implicated in a wide variety of diseases, including cancer, AIDS, diabetes mellitus, cardiovascular diseases, autoimmune diseases, viral replication, septic shock, neurodegenerative disorders, ataxia telangiectasia (AT), arthritis, asthma, inflammatory bowel disease, and other inflammatory conditions, atherosclerosis, heart disease, asthma, catabolic disorders, type 1 and 2 diabetes, ageing, skin diseases, renal diseases, gut diseases, pancreatitis, neuropathological diseases, pulmonary diseases, chronic obstructive pulmonary disease, sepsis and sleep apnea. The activation of NF-κB has been implicated in a large number of human diseases.

For example, activation of NF-κB by Gram-negative bacterial lipopolysaccharides (LPS) may contribute to the development of septic shock because NF-κB over-activates the transcription of numerous cytokines and modifying enzymes, whose prolonged expression can negatively effect the function of vital organs such as the heart and liver (Arcaroli et al., 2006; Niu et al., 2008).

Additionally, in chronic Alzheimer's disease, the amyloid β peptide causes production of reactive oxygen intermediates and indirectly activates gene expression through NF-κB sites (Giri et al., 2005).

Destructive erosion of bone or osteolysis is a major complication of inflammatory conditions such as rheumatoid arthritis (RA), periodontal disease, and periprosthetic osteolysis. RA is an autoimmune disease that affects approximately 1.0% of US adults, with a female to male ratio of 2.5 to 1 (Lawrence et al., 1998). Its hallmark is progressive joint destruction which causes major morbidity. Periodontal disease is highly prevalent and can affect up to 90% of the world's population. It is well known as the leading cause of tooth loss in adults (Pihlstrom et al., 2005). Despite its prevalence, little is known about the mechanism by which periodontal bone erosion occurs, although host response to pathogenic microorganisms present in the mouth appears to trigger the process. Periprosthetic osteolysis is caused by chronic bone resorption around exogenous implant devices until fixation is lost (Harris, 1995), and is considered as resulting from an innate immune response to wear-debris particles, with little contribution by components of the acquired immune system (Goldring et al., 1986).

Although these conditions are initiated by distinct causes and progress by alternative pathways, the important common factor(s) in the pathological process of these diseases are over-production of proinflammatory cytokines which is driven by the constitutive activation of the NF-κB pathway in the inflamed tissue. The bone erosion seen in these conditions is largely localized to the inflamed tissues, distinct from systemic, hormonally regulated bone pathologies, such as osteoporosis. These inflamed tissues, found in many of these diseases, also produce proinflammatory cytokines, i.e., TNF-α, IL-1, and IL-6, that are, in turn, involved in osteoclast differentiation signaling and bone-resorbing activities. Thus, inflammatory osteolysis is the product of enhanced osteoclast recruitment and activation prompted by NF-κB driven proinflammatory cytokines in the inflamed tissue.

Inflammatory bowel disease (IBD) encompasses a number of chronic relapsing inflammatory disorders involving the gastrointestinal tract. The two most prevalent forms of IBD, Crohn's disease and ulcerative colitis, can be distinguished by unique histopathologies and immune responses (Atreya et al., 2008; Bouma & Strober, 2003). The limited efficacy and potential adverse effects of current treatments leave patients and doctors eager for new treatments to manage the chronic relapsing inflammatory nature of these diseases.

Although the exact aetiologies leading to Crohn's disease and ulcerative colitis remain unknown, they are generally thought to result from an inappropriate and ongoing activation of the mucosal immune system against the normal luminal flora (Tilg et al., 2008). As a result, resident macrophages, dendritic cells and T cells are activated and begin to secrete predominantly NF-κB-dependent chemokines and cytokines. NF-κB mediated overproduction of key pro-inflammatory mediators is attributed to the initiation and progression of both human IBD and animal models of colitis (Neurath et al., 1998; Wirtz & Neurath, 2007). In particular, macrophages of patients with IBD exhibit high levels of NF-κB DNA binding activity accompanied by increased production of interleukin (IL)1, IL6 and tumour necrosis factor (TNFα) (Neurath et al., 1998). In addition, NF-κB plays a vital role in activating T helper cell 1 (Th1) and T helper cell 2 (Th2) cytokines, both of which are required for promoting and maintaining inflammation (Barnes, 1997). Because of the central role played by NF-κB in IBD, extensive efforts have been made to develop treatments targeting this pathway.

NF-κB has been shown to be constitutively expressed in numerous cancer derived cell lines from breast, ovarian, colon, pancreatic, thyroid, prostate, lung, head and neck, bladder, and skin tumors (Calzado et al., 2007). This has also been seen for B-cell lymphoma, Hodgkin's disease, T-cell lymphoma, adult T-cell leukemia, acute lymphoblastic leukemia, multiple myeloma, chronic lymphocytic leukemia, and acute myelogenous leukemia. Although NF-κB is a key mediator of normal inflammation as part of the defense response, chronic inflammation can lead to cancer, diabetes, and a host of other diseases as mentioned above. Several pro-inflammatory gene products have been identified that mediate a critical role in the carcinogenic process, angiogenesis, invasion, and metastasis of tumor cells. Among these gene products are TNF and members of its superfamily, IL-1α, IL-1β, IL-6. IL-8, IL-18, chemokines, MMP-9, VEGF, COX-2, and 5-LOX. The expression of all these genes are mainly regulated by the transcription factor NF-κB, which is constitutively active in most tumors and is induced by carcinogens (such as cigarette smoke), tumor promoters, carcinogenic viral proteins (HIV-tat, KHSV, EBV-LMP1, HTLV1-tax, HPV, HCV, and HBV), chemotherapeutic agents, and gamma-irradiation (Aggarwal et al., 2006). These observations imply that anti-inflammatory agents that suppress NF-κB should have a potential in both the prevention and treatment of cancer.

The influenza virus protein hemagglutinin also activates NF-κB, and this activation may contribute to viral induction of cytokines and to some of the symptoms associated with influenza (Flory et al., 2000; Pahl & Baeuerle, 1995).

Oxidized lipids from the low density lipoproteins associated with atherosclerosis activate NF-κB, which then activates other genes such as inflammatory cytokines (Liao et al., 1994). Furthermore, mice that are susceptible to atherosclerosis, exhibit NF-κB activation when fed an atherogenic diet, due to their susceptibility to aortic atherosclerotic lesion formation associated with the accumulation of lipid peroxidation products, induction of inflammatory genes, and the activation of NF-κB transcription factors (Liao et al., 1994). Another important contributor to atherosclerosis is thrombin, which stimulates the proliferation of vascular smooth muscle cells through the activation of NF-κB (Maruyama et al., 1997). A truncated form of IκB repressor protein (IκBα) was shown to be the cause of the hypersensitivity to ionizing radiation and is defective in the regulation of DNA synthesis in ataxia telangiectasia (AT) cells, which have constitutive levels of NF-κB-activation (Jung et al., 1995). This mutation in IκBα from the AT cells was shown to inactivate the repressor protein causing the constitutive activation of the NF-κB pathway. In light of all these findings, the abnormal activation or expression of NF-κB is clearly associated with a wide variety of pathologic conditions.

The infection and life-cycle of HIV-1 is tightly coupled to the NF-κB pathway in human mononuclear cells. Viral infection leads to the activation of NF-κB which generates the over stimulation and eventual depletion of T-cells that is the hallmark of AIDS (reviewed in (Argyropoulos & Mouzaki, 2006). For instance, the expression of CCR5, a key receptor for HIV-1, is regulated by NF-κB (Liu et al., 1998). Deletion analysis of the CCR-5 promoter has demonstrated that loss of the 3'-distal NF-κB/AP-1 site drops transcription by >95% (Liu et al., 1998). These studies would suggest that constitutive repression of NF-κB would cause a dramatic decrease in CCR-5 receptor message. Since HIV-1 entry kinetics are influenced by expressed levels of CCR5 on the target T-cell surface (Ketas et al., 2007; Platt et al., 1998; Reeves et al., 2002), down modulating CCR5 may constrain the expansion of the pool of infected cells that spawns the viral reservoir. CXCR4 expression has also been reported to be influenced by NF-κB (Helbig et al., 2003) suggesting that NF-κB inhibitors may be equally effective against X4-tropic isolates that appear during late-stage infection. NF-κB is required for transcription of the integrated DNA-pro-virus (Baba, 2006; Iordanskiy et al., 2002; Mukerjee et al., 2006; Palmieri et al., 2004; Rizzi et al., 2004; Sui et al., 2006; Williams et al., 2007). In fact, lack of NF-κB activation leads to the generation of a population of cells harboring latent virus which is a major block to eliminating the virus from infected patients (Williams et al., 2006).

NF-κB promotes the expression of over 150 target genes in response to inflammatory stimulators. These genes include interleukin-1, -2, -6 and the tumor necrosis factor receptor (TNF-R) (these receptors mediate apoptosis, and function as regulators of inflammation), as well as genes encoding immunoreceptors, cell adhesion molecules, and enzymes such as cyclooxygenase-II and inducible nitric oxide synthase (iNOS) (Karin, 2006; Tergaonkar, 2006). It also plays a key role in the progression of diseases associated with viral infections such as HCV and HIV-1.

Members of the NF-κB family include RelA/p65, RelB, c-Rel, p50/p105 (NF-κB)), and p52/p100 (NF-κB2) (Hayden & Ghosh, 2004; Hayden et al., 2006a; Hayden et al., 2006b). The Rel family members function as either homodimers or heterodimers with distinct specificity for cis-binding elements located within the promoter domains of NF-κB-regulated genes (Bosisio et al., 2006; Natoli et al., 2005; Saccani et al. 2004). Classical NF-κB, composed of the RelA p65 and p50 heterodimer, is the best-studied form of NF-κB (Burstein & Duckett, 2003; Hayden & Ghosh, 2004) and references therein). Prior to cellular stimulation, classical NF-κB resides in the cytoplasm as an inactive complex bound to the IκBα inhibitor proteins. Inducers of NF-κB such as bacterial lipopolysaccharides, inflammatory cytokines, or HIV-1 Vpr protein release active NF-κB from the cytoplasmic complex by activating the IκB-kinase complex (IKK), which phosphorylates IκBα (Greten & Karin, 2004; Hacker & Karin, 2006; Israel, 2000; Karin, 1999; Scheidereit, 2006). Phosphorylation of IκB marks it for subsequent ubiquitinylation and degradation by the 26S proteosome. Free NF-κB dimers translocate into the nucleus where they stimulate the transcription of their target genes.

The molecular design of racemic dehydroxymethylepoxyquinomicin (DHMEQ) was based on the antibiotic epoxyquinomicin C isolated from *Amycolatopsis* (Chaicharoenpong et al. 2002). DHMEQ was synthesized as a racemate from 2,5-dimethoxyaniline in five steps. Separation of the enantiomers on a chiral column produced both (+) and (−) enantiomers. The (−)-enantiomer was shown to be more potent at inhibiting NF-κB than the (+)-enantiomer (Umezawa et al. 2004). DHMEQ has been shown to specifically inhibit the translocation of NF-κB into the nucleus (Ariga et al. 2002). Specifically, it covalently modifies a specific cysteine residue in p65 and other Rel homology proteins with a 1:1 stoichiometry ratio (Yammamoto et al. 2008). As an NF-κB inhibitor, DHMEQ has been tested extensively in various animal models of diseases and has demonstrated a broad spectrum of efficacy including treating solid tumors, hematological malignancy, arthritis, bowel ischemia, and atherosclerosis (Watanabe et al. 2006). Thus, DHMEQ may be useful as a treatment for cancer and inflammation (Takeuchi et al. 2003).

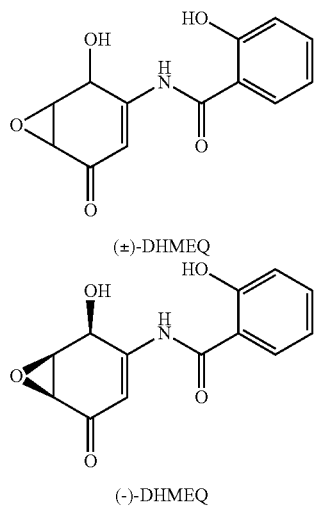

(±)-DHMEQ (−)-DHMEQ

In view of the role that activation of NF-κB plays in a number of diverse diseases, such as those described above, there is an ongoing need for effective small-molecule NF-κB inhibitors.

Several series of small molecule inhibitors have been discovered that directly inhibit the binding of NF-κB components, p65 (RelA), RelB and c-Rel to DNA. As a result, these compounds can block both the canonical and the noncanonical paths of NF-κB. The dual inhibition is distinct from IκBβ kinase inhibitors that affect only the canonical path. The efficacies of the compounds have been tested in animal models of multiple myeloma and rheumatoid arthritis and the results are described herein.

SUMMARY OF THE INVENTION

An aspect of the present invention relates to compounds having the structure of formula (1) or formula (2)

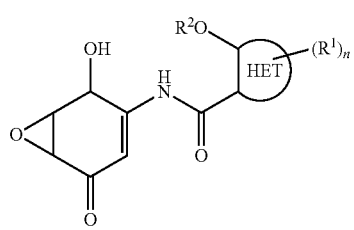

(1)

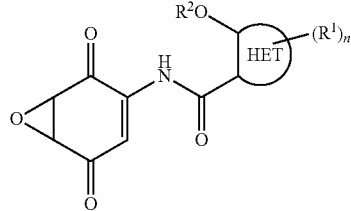

(2)

or a pharmaceutically acceptable salt thereof, wherein HET is a saturated or unsaturated mono- or multi-ring carbocycle in which one or more of the ring carbon atoms is replaced by N, S, P or O;

Each $R^1$ is independently hydrogen; $CF_3$; phenyl optionally substituted with cyano, halo, nitro, hydroxyl, (C1-C6)alkyl, (C1-C6)alkyl-OH, (C1-C6)alkoxy, $COR^3$, $NR^4R^5$ or $NHCO$(C1-C6)alkyl); cyano; halo; nitro; hydroxyl; (C1-C6)alkyl; (C1-C6)alkyl-OH; (C1-C6)alkoxy; (C1-C6)thioalkoxy; phenoxy; $COR^3$; $NR^4R^5$; $NHCO$(C1-C6)alkyl; $SO_2$(C1-C6) alkyl; or $SO_2NR^4R^5$.

$R^2$ is H, $R^6$, $COR^6$, $CONHR^6$, $COOR^6$, $CH_2OCOR^6$, $P(O)(OH)_2$, $P(O)(O$(C1-C6)alkyl$)_2$, $P(O)(OCH2OCO$(C1-C6)alkyl$)_2$, $P(O)(OH)(OCH2OCO$(C1-C6)alkyl), $P(O)(OH)(O$(C1-C6)alkyl), $P(O)(OH)$(C1-C6)alkyl), an inorganic salt of $P(O)(OH)_2$, $P(O)(O$(C1-C6)alkyl$)_2$, $P(O)(OCH_2OCO$(C1-C6)alkyl$)_2$, $P(O)(OH)(OCH_2OCO$(C1-C6)alkyl), $P(O)(OH)$ $(OC1-C6)alkyl$) or $P(O)(OH)$(C1-C6)alkyl), or glycosyl (the radical resulting from the removal of a hydroxyl group of the hemiacetal form of a carbohydrate), wherein $R^6$ is C1-C6 alkyl, trifluoromethyl, (C3-C6) cycloalkyl, cyclohexylmethyl or phenyl, wherein the phenyl is substituted with 0 to 4 groups selected from fluorine, chlorine, bromine, hydroxyl, trifluoromethyl, (C1-C4)alkyl, (C1-C4)alkoxy and phenylmethyl, wherein the phenylmethyl is substituted on the phenyl ring with 0-4 groups selected from fluorine, chlorine, bromine, hydroxyl, trifluoromethyl, (C1-C4)alkyl, (C1-C4)alkoxy, 2-, 3-, or -4-pyridinyl and 2-, -4-, or 5-pyrimidinyl.

$R^3$ is independently hydroxyl, (C1-C6)alkoxy, phenoxy or —$NR^4R^5$.

Each $R^4$ and $R^5$ is independently hydrogen, (C1-C6)alkyl or (C3-C6)cycloalkyl.

n=0-3.

On HET, there exists an ortho relationship between the $OR^2$ group and the amide moiety (i.e., the $OR^2$ and the C(═O)NH functionalities are attached to adjacent atoms on the HET ring).

An aspect of the present invention also relates to a pharmaceutical composition comprising a compound of formula (1) or formula (2), or a pharmaceutically acceptable salt thereof, and a pharmaceutically acceptable carrier.

An aspect of the present invention further relates to a method of treating cancer, inflammation, auto-immune diseases, diabetes and diabetic complications, infection, cardiovascular disease and ischemia-reperfusion injuries, comprising administering to a mammal in need of such treatment, such as a human, a therapeutically effective amount of a compound of formula (1) or formula (2), or a pharmaceutically acceptable salt thereof.

An aspect of the present invention additionally relates to a method of inhibiting gene expression and signal transduction directly or indirectly through the NF-κB pathway in a mammal, such as a human, comprising administering to a mammal in need of such a treatment a therapeutically effective amount of a compound of formula (1) or formula (2), or a pharmaceutically acceptable salt thereof.

BRIEF DESCRIPTION OF THE FIGURES

The figures represent specific embodiments of the described invention and are therefore used for illustrative purposes only. Accordingly, the figures are not intended to limit the scope of the invention.

FIG. 11 shows that the compound of Example 2 (at 10 uM) does not interact with human P450s and hERG (<50% inhibition).

DETAILED DESCRIPTION

Definitions

Figure 1:
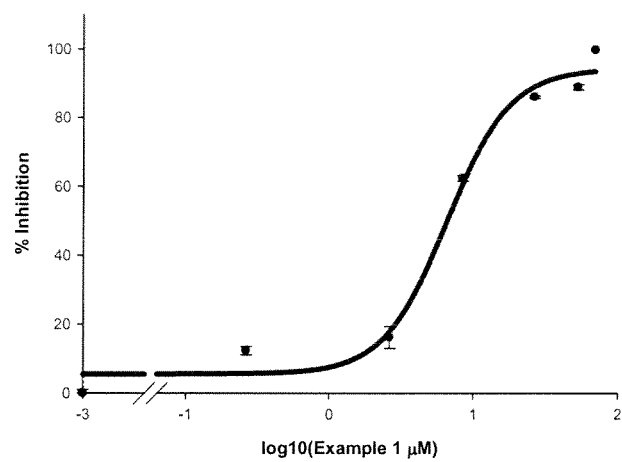
FIG. 1 shows the concentration dependent inhibition of expression of two NF-κB dependent reporter genes, luciferase (A) and green fluorescence protein (GFP) (B) by the compound of Example 1 in HEK-293 cells.
Figure 1:
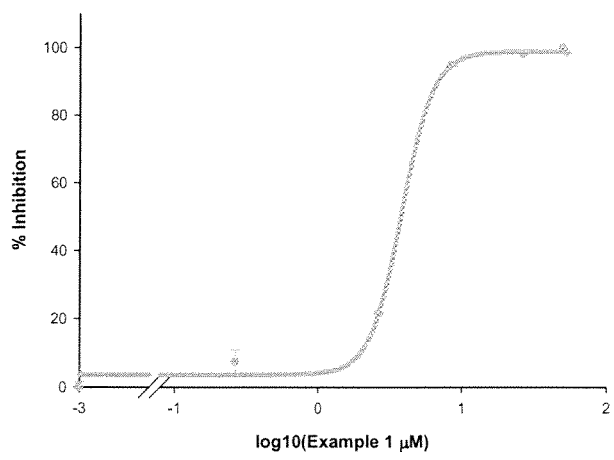

The terms used to describe the present invention have the following meanings herein. The compounds and intermediates of the present invention may be named according to either the IUPAC (International Union for Pure and Applied Chemistry) or CAS (Chemical Abstracts Service) nomenclature systems.

The carbon atom content of the various hydrocarbon-containing moieties herein may be indicated by a prefix designating the minimum and maximum number of carbon atoms in the moiety, for example, the prefix (Ca-Cb)alkyl indicate an alkyl moiety of the integer "a" to "b" carbon atoms, inclusive. Thus, for example, (C1-C6)alkyl refers to an alkyl group of one to six carbon atoms inclusive. The term "alkyl" denotes a straight or branched chain of carbon atoms with only hydrogen atom substituents, wherein the carbon chain optionally contains one or more double or triple bonds, or a combination of double bonds and triple bonds. Examples of alkyl groups include, but are not limited to, methyl, ethyl, propyl, isopropyl, propenyl, propynyl, hexadienyl, and the like.

The term "alkoxy" refers to straight or branched, monovalent, saturated aliphatic chains of carbon atoms wherein one of the carbon atoms has been replaced with an oxygen atom. Examples of alkoxy groups include, but are not limited to, methoxy, ethoxy and iso-propoxy.

The term "cycloalkyl" refers to a saturated and optionally unsaturated monocyclic or bicyclic arrangement of aliphatic chains. Examples of cycloalkyl groups include, but are not limited to, cyclopropyl, cyclobutyl, cyclopentyl and cyclohexenyl. Cycloalkyl groups may also be optionally fused to aromatic hydrocarbons such as benzene to form fused cycloalkyl groups, such as indanyl and the like.

The term "halo" refers to chloro, bromo, fluoro, or iodo.

The term "substituted" refers to replacement of a hydrogen atom on a molecule with a different atom or molecule. The atom or molecule replacing the hydrogen atom is denoted as a "substituent."

The term "HET" refers to a saturated or unsaturated mono- or multi-ring carbocycle in which one or more of the ring carbon atoms are replaced by N, S, P or O. The term "HET" is intended to encompass fully saturated and unsaturated ring systems as well as partially unsaturated ring systems, including all possible isomeric forms of the heterocycle (for example, pyrrolyl comprises 1H-pyrrolyl and 2H-pyrrolyl). Examples of where HET is a monocyclic (e.g., a 4-, 5- or 6-membered ring) or a bicyclic (e.g., a 5/6, 5/5, 6/6 system) saturated heterocycle include, but are not limited to, tetrahydrofuranyl, pyrrolidinyl, tetrahydrothienyl, dihydrooxazolyl, piperidinyl, hexahydropyrimidinyl, dioxanyl, morpholinyl, dithianyl, thiomorpholinyl, piperazinyl and the like. Examples of where HET is a monocyclic, bicyclic or tricyclic partially saturated heterocycle include, but are not limited to, pyrrolinyl, imidazolinyl, pyrazolinyl, 2,3-dihydrobenzofuranyl, 1,3-benzodioxolanyl, 2,3dihydro-1,4-benzodioxinyl, indolinyl and the like. Examples of where HET is a monocyclic, bicyclic or tricyclic aromatic heterocycle include, but are not limited to, pyrrolyl, furanyl, thienyl, imidazolyl, oxazolyl, isoxazolyl, thiazolyl, isothiazolyl, pyrazolyl, 1,2,3-triazolyl, 1,2,5-thiadiazolyl, 1,2,3-thiadiazolyl, 1,2,3-oxadiazolyl, 1,2,5-oxadiazolyl, pyridinyl, pyrimidinyl, pyrazinyl, pyridazinyl, triazinyl, benzofuranyl, isobenzofuranyl, benzothienyl, isobenzothienyl, indolizinyl, indolyl, isoindoly, benzoxazolyl, benzimidazolyl, indazolyl, benzisoxazolyl, benzisothiazolyl, benzopyrazolyl, benzoxadiazolyl, benzothiadiazolyl, benzotriazolyl, quinolinyl, isoquinolinyl, cinnolinyl, quinolizinyl, phthalazinyl, quinoxalinyl, quinazolinyl, naphthyridinyl, pteridinyl, pyrrolopyridinyl, thienopyridinyl, furanopyridinyl, isothiazolopyridinyl, thiazolopyridinyl, isoxazolopyridinyl, oxazolopyridinyl, pyrazolopyridinyl, imidazopyridinyl, pyrrolopyrazinyl, thienopyrazinyl, furanopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furanopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furanopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridinyl, thiadiazolopyridinyl, triazolopyridinyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl and the like.

The phrase "therapeutically effective amount" refers to an amount of a compound that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition.

The phrase "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "mammal" relates to an individual animal that is a member of the taxonomic class Mammalia. Examples of mammals include, but are not limited to, humans, dogs, cats, horses and cattle. In the present invention, the preferred mammal is a human.

Racemic compound 2-hydroxy-N-(2-hydroxy-5-oxo-7-oxabicyclo[4.1.0]hept-3-en-3-yl)quinoline-3-carboxamide is described in Example 2 herein and is referred to throughout as the compound of Example 2.

In an exemplary embodiment, the compounds of the present invention have the structure and the stereochemistry shown in formula (3).

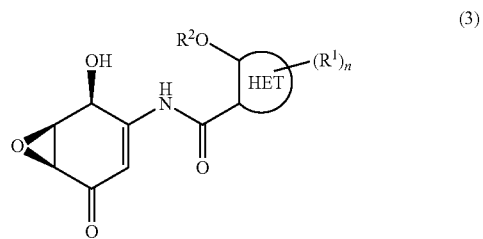

(3)

The compounds may be resolved into their enantiomers by methods well known to those skilled in the art. Examples include formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, enzymatic etherification; or gas-liquid or liquid chromatography in a chiral environment, for example, on a chiral support for example silica with a bound chiral ligand or in the presence of a chiral solvent. It will be appreciated that where the desired stereoisomer is converted into another chemical entity by one of the exemplary separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Wherein the compounds contain one or more additional stereogenic centers, those skilled in the art will appreciate that all diastereoisomers and diastereoisomeric mixtures of the compounds illustrated and discussed herein are within the scope of the present invention. These diastereoisomers may be isolated by methods well known to those skilled in the art, for example, by crystallization, gas-liquid or liquid chromatography. Alternatively, intermediates in the course of the synthesis may exist as racemic mixtures and be subjected to resolution by methods well known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, enzymatic esterification; or gas-liquid or liquid chromatography in a chiral environment, for example, on a chiral support for example silica with a bound chiral ligand or in the presence of a chiral solvent. It will be appreciated that where the desired stereoisomer is converted into another chemical entity by one of the exemplary separation procedures described above, a further step is required to liberate the desired enantiomeric form. Alternatively, the specific stereoisomers may be synthesized by using an optically active starting material, for example, by asymmetric synthesis using optically active reagents, substrates, catalysts or solvents, or by converting one stereoisomer into the other by asymmetric transformation. These methods are described in more detail in texts such as "Chiral Drugs", Cynthia A. Challener (Editor), Wiley, 2002 or "Chiral Drug Separation" by Bingyunh Li and Donald T. Haynia in "Encyclopedia of Chemical Processing" by Sunggyu Lee and Lee Lee (Editors), CRC Press, 2005.

The compounds of the present invention, and the salts thereof, may exist in the unsolvated as well as the solvated forms with pharmaceutically acceptable solvents such as water, ethanol, and the like.

Selected compounds of formula (1) and formula (2) and their salts and solvates may exist in more than one crystal form. Polymorphs of compounds represented by formula (1) and formula (2) form part of this invention and may be prepared by crystallization of a compound of formula (1) or formula (2) under different conditions. Examples include using different solvents or solvent mixtures for recrystallization; crystallization at different temperatures; and various modes of cooling, ranging from very fast to very slow cooling during crystallization. Polymorphs may also be obtained by heating or melting a compound of formula (1) or formula (2) followed by gradual or fast cooling. The presence of polymorphs may be determined by, for example, solid state NMR spectroscopy, IR spectroscopy, differential scanning calorimetry, powder X-ray diffraction or other such techniques.

This invention also includes isotopically-labeled compounds, which are identical to those described by formulas (1) and (2), but for the fact that one or more atoms have been replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$ and $^{18}F$ respectively. Compounds of the present invention and pharmaceutically acceptable salts of the compounds which contain the aforementioned isotopes and/or other isotopes of other atoms are within the scope of this invention. Certain isotopically-labeled compounds of the present invention, for example those into which an isotope such as $^2H$ (deuterium) have been incorporated can afford therapeutic advantages resulting from greater metabolic stability, for example, increased in vivo half life or reduced dosage requirements and, hence, may be preferred in some circumstances. Isotopically labeled compounds of formulas (1) and (2) of this invention, salts and solvates thereof can generally be prepared by carrying out procedures disclosed in the schemes and/or in the Examples below, by substituting a readily available isotopically labeled reagent for a non-isotopically labeled reagent.

Pharmaceutically acceptable salts, as used herein in relation to compounds of the present invention, include pharmaceutically acceptable inorganic and organic salts of said compounds. These salts can be prepared in situ during the final isolation and purification of a compound, or by separately reacting the compound with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, camsylate, palmitate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. Compounds of the present invention may also react to form salts with pharmaceutically acceptable metal and amine cations formed from organic and inorganic bases. The term "pharmaceutically acceptable metal cation" contemplates positively charged metal ions derived from sodium, potassium, calcium, magnesium, aluminum, iron, zinc and the like. The term "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art. (See, for example, Berge, et al., "Pharmaceutical Salts," *J. Pharm. Sci.*, 66:1-19 (1977)).

The present invention further includes prodrugs of compounds of formula (1). A prodrug of a compound of formula (I) may be fowled in a conventional manner with a functional group of the compound, such as with an amino, hydroxy or carboxy group. The term "prodrug" refers to a compound that is transformed in vivo to yield a compound of formula (I) or formula (II) or a pharmaceutically acceptable salt or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound of the present invention contains an alcohol functional group, a prodrug can be formed by the replacement of the hydrogen atom of the alcohol group with a group such as $COR^6$ to provide an ester prodrug; with $CONHR^6$ to provide a carbamate prodrug; with $COOR^6$ to provide a carbonate prodrug; with $CH_2OCOR^6$ to provide an alkylcarbonyloxymethyl prodrug; with $P(O)(OH)_2$ to provide a phosphate prodrug; with $P(O)(O(C1-C6)alkyl)_2$ to provide a phosphate prodrug; with $P(O)(OCH2OCO(C1-C6)alkyl)_2$ to provide a phosphate prodrug; with $P(O)(OH)(OCH2OCO(C1-C6)alkyl)$ to provide a phosphate prodrug; with $P(O)(OH)(OC1-C6)alkyl)$ to provide a phosphate prodrug; or with $P(O)(OH)(C1-C6)alkyl)$ to provide a phosphonate prodrug, and the corresponding inorganic salts of the phosphate and phosphonate prodrugs, or glycosyl (the radical resulting from the removal of a hydroxyl group of the hemiacetal form of a carbohydrate), wherein $R^6$ is C1-C6 alkyl, trifluoromethyl, cyclopropyl, cyclohexyl, cyclohexylmethyl, phenyl, phenyl substituted with fluorine, chlorine, bromine, hydroxyl, trifluoromethyl, (C1-C4)alkyl, (C1-C4)alkoxy, phenylmethyl, phenylmethyl substituted with fluorine, chlorine, bromine, hydroxyl, trifluoromethyl, (C1-C4)alkyl, (C1-C4)alkoxy, 2-, 3-, or -4-pyridinyl, 2-, -4-, or 5-pyrimidinyl.

There was a focus on targeting a "down-stream" event of NF-κB activation, preventing p65, RelB and c-Rel from binding to DNA enhancer sequences and activating transcription. This approach made it possible to modulate both canonical and non-canonical pathways, either together or separately with different compounds. In addition, the "down-stream" NF-κB inhibitors may avoid the side effects observed for many "up-stream" NF-κB inhibitors. A drug screening paradigm has been established to identify novel and proprietary NF-κB inhibitors of the Rel family. Three parallel approaches have been taken to identify suitable lead molecules: (1) an in-silico screen of 5,000,000 compounds using the crystal structure of p65, (2) a broad high-throughput screen of a diversified compound library using a cell based screen, and (3) modification to improve existing inhibitors of p65. In comparison to known p65 antagonists, e.g., the natural product pathenolide and the synthetic molecule, dehydroxymethylepoxyquinomicin (DHMEQ), the compounds of the invention display a significant improvement in potency against p65 (RelA) (see FIG. 7).

Unlike DHMEQ or pathenolide, the compounds of the invention have been discovered to also inhibit RelB (see FIG. 8) and c-Rel (Table 1). Thus, the compounds are dual inhibitors of canonical and non-canonical paths, as well as sole inhibitors.

In general, compounds of the present invention are prepared by the general synthetic methods outlined in Reaction Schemes 1 and 2, where "R" as indicated in the schemes is the moiety shown below

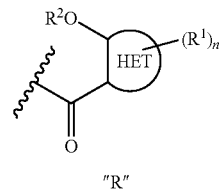

"R"

and HET is as described herein.

Referring to Reaction Scheme 1, compounds 2-5 can be prepared according to published literature procedures (see, e.g., Taylor et al., *Synthesis* 1998, 775). Treatment of 2,5-dimethoxyaniline 1 with di-tert-butyl dicarbonate ($Boc_2O$) and triethylamine in methanol or tetrahydrofuran at temperatures ranging from 0° C. to room temperature gave the protected aniline derivative 2. Oxidation with bis(acetoxyiodo) benzene in methanol at 0° C. gave the ketal 3. Monoepoxidation to yield 4 was achieved using 30% aqueous hydrogen peroxide and a base such as aqueous sodium hydroxide or potassium carbonate in aqueous tetrahydrofuran at temperatures ranging from 0° C. to room temperature. Selective removal of the Boc group with a 4/1 dichloromethane/trifluoroacetic acid mixture at temperatures ranging from 0° C. to room temperature gave the free amine 5. Alternatively, this deprotection can be achieved using boron trifluoride-diethyl ether complex and activated molecular sieves in a solvent such as dichloromethane at room temperature. The amine 5 was then coupled with an acid chloride (RCl) using a base such as lithium tert-butoxide ($LiO^tBu$) in a solvent such as anhydrous tetrahydrofuran at −78° C. to give the ketal 6. The various acid chlorides (RCl) were prepared from the corresponding carboxylic acid by refluxing in neat thionyl chloride. The ketal 6 was de-protected in an acidic media such as trifluoroacetic acid in a solvent such as dichloromethane at temperatures ranging from 0° C. to room temperature to give diketone 7. Regioselective reduction of 7 was achieved by treatment with a slight excess of a mild reducing agent such as sodium triacetoxyborohydride ($NaBH(OAc)_3$) in a solvent such as methanol at temperatures ranging from 0° C. to room temperature.

An alternative synthetic route is depicted in Reaction Scheme 2. Treatment of 2,5-dimethoxyaniline 1 with an acid chloride (RCl) and a base such as pyridine in a solvent such as anhydrous tetrahydrofuran at temperatures ranging from 0° C. to room temperature gave 10. Oxidation with bis(acetoxyiodo) benzene in methanol at 0° C. gave the ketal 11. Monoepoxidation to yield 6 was achieved using 30% aqueous hydrogen peroxide and a base such as aqueous sodium hydroxide at temperatures ranging from 0° C. to room temperature. The ketal 6 was deprotected in an acidic media such as trifluoroacetic acid in a solvent such as dichloromethane at temperatures ranging from 0° C. to room temperature to give diketone 7. Regioselective reduction of 7 to provide 8 was achieved by treatment with a slight excess of a mild reducing agent such as sodium triacetoxyborohydride ($NaBH(OAc)_3$) in a solvent such as methanol at temperatures ranging from 0° C. to room temperature.

It was discovered that the diketone intermediates of the general formula (7) as depicted in Reaction Scheme (2) also exhibited significant activity as NF-κB inhibitors. Thus, diketones of general formula (2) as described herein are considered as part of the invention.

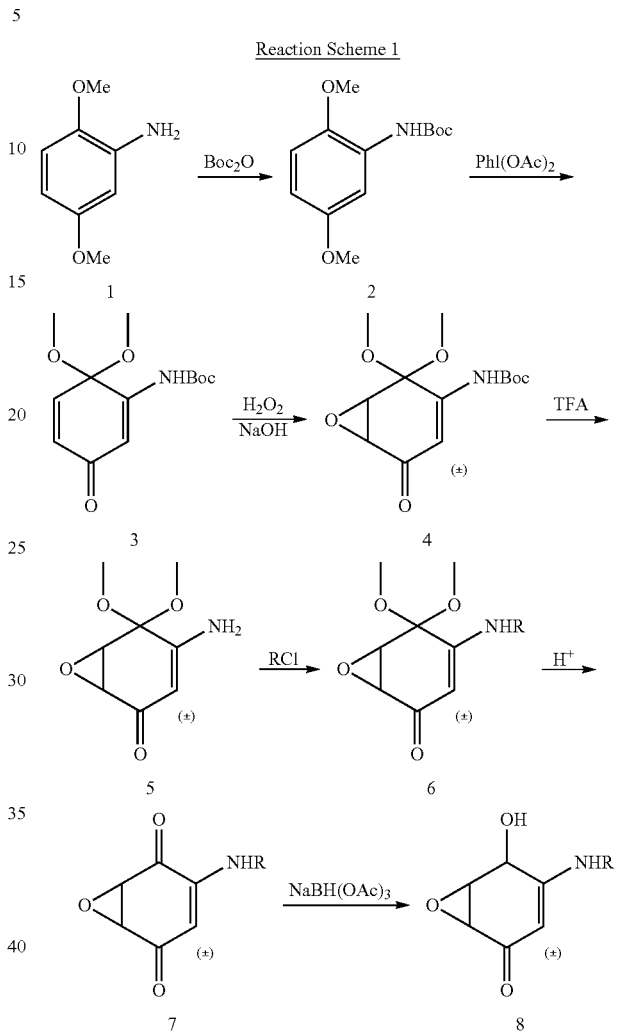

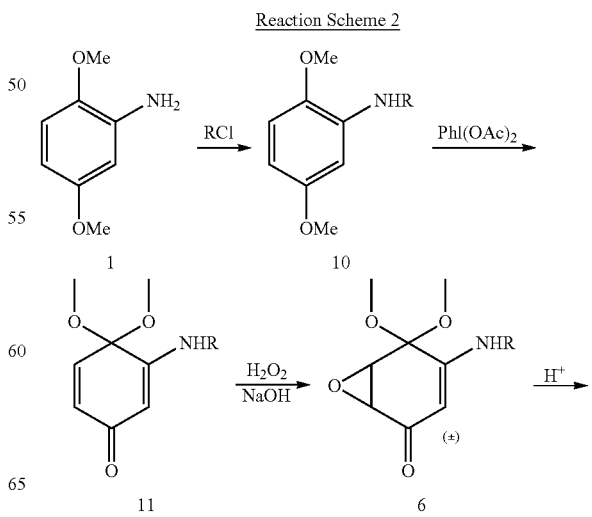

-continued

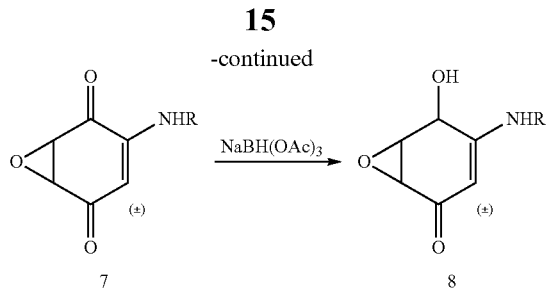

A pharmaceutical composition of the present invention comprises a therapeutically effective amount of a compound of formula (1), or a pharmaceutically acceptable salt thereof, and a pharmaceutically acceptable carrier, vehicle, diluent or excipient. A preferred pharmaceutical composition of the present invention comprises a therapeutically effective amount of a compound of formula (2), or a pharmaceutically acceptable salt thereof, and a pharmaceutically acceptable carrier, vehicle, diluents or excipient. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like.

Thus, for purposes of oral administration, tablets containing various excipients such as sodium citrate, calcium carbonate and/or calcium phosphate, may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions of elixirs are desired for oral administration, the active pharmaceutical agent therein may be combined with various sweetening of flavoring agents, coloring matter or dyes and, if desired, emulsifying or, suspending agents, together with diluents such as water, ethanol, propylene glycol, glycerin and/or combinations thereof.

For parenteral administration, solutions of the compounds or compositions of this invention in sesame or peanut oil, aqueous propylene glycol, or in sterile aqueous solutions may be employed. Such aqueous solutions should be suitably buffered if necessary and the liquid diluents first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

In an exemplary embodiment, the pharmaceutical preparation is in unit dosage form. In such form, the preparation is subdivided into unit doses containing appropriate quantities of the active component. The unit dosage form can be a packaged preparation, for example, packeted tablets, capsules, and powders in vial or ampoules. The unit dosage form can also be a capsule, cahet, or tablet itself or it can be the appropriate number of any of these packaged forms.

Methods of preparing various pharmaceutical compositions with a certain amount of active ingredient are known to those skilled in the art. For examples of methods of preparing pharmaceutical compositions, see Remington: *The Science and Practice of Pharmacy*, Lippincott, Williams & Wilkins, 21$^{st}$ ed. (2005), which is incorporated by reference in its entirety.

In one embodiment of the invention, the compounds of the invention may also be combined with at least one additional therapeutic agent.

EXAMPLES

Example 1

Preparation of (±)-2-hydroxy-N-(2-hydroxy-5-oxo-7-oxabieyelo[4.1.0]hept-3-en-3-yl)nicotinamide (8a)

A. Preparation of tert-butyl 2,5-dimethoxyphenylcarbamate (2)

To a solution of 2,5-dimethoxyaniline 1 (50 g, 326 mmol) in MeOH (1 L) in an ice bath under an inert nitrogen atmosphere was added triethylamine (55 mL, 397 mmol), followed by the drop-wise addition of Boc$_2$O (78 g, 359 mmol) in methanol (150 mL). The reaction was stirred overnight. After judging incomplete by thin layer chromatography, additional Boc$_2$O (22 g, 69 mmol) and triethylamine (55 mL, 397 mmol) was added and the solution was stirred 3 days. The methanol was removed and the residue was dissolved in ethyl acetate, which was rinsed with diluted hydrochloric acid (2×) and brine before drying over anhydrous magnesium sulfate, followed by filtration, and solvent evaporation to afford 50 g (61%) tert-butyl 2,5-dimethoxyphenylcarbamate (2) as a brown oil. The $^1$H NMR was consistent with that reported in the literature (*Synthesis* 1998, 775).

B. Preparation of tert-butyl 6,6-dimethoxy-3-oxocyclohexa-1,4-dienylcarbamate (3)

A methanolic (700 mL) solution of compound 2 (29 g, 115 mmol) was cooled in an ice bath before the addition of bis (acetoxyiodo) benzene (62 g, 194 mmol) in six portions over a period of 30 minutes. The solution was stirred in the ice bath for 2 hours then brought to room temperature and stirred overnight. The reaction mixture was diluted with ethyl acetate (1.5 L) and rinsed with water, dilute hydrochloric acid, and brine. The aqueous was back-extracted once with ethyl acetate and the organics combined before drying over anhydrous magnesium sulfate, followed by filtration, and solvent evaporation. The resulting liquid was purified over silica gel using a gradient of ethyl acetate (0 to 2%) in heptane, giving 6.9 g (21%) (3) as a yellow-orange solid. Material was sufficiently pure (approx. 95%) by $^1$H NMR, which was consistent with that reported in the literature (Synthesis 1998, 775).

C. Preparation of tert-butyl 2,2-dimethoxy-5-oxo-7-oxabicyclo[4.1.0]hept-3-en-3-ylcarbamate (4)

Compound 3 (3.4 g, 12.7 mol) in tetrahydrofuran (93 mL) was cooled in an ice bath. To the stirring solution, in drop-wise fashion, was added hydrogen peroxide (30% aq., 22 mL) and aqueous sodium hydroxide (1M, 61 mL) in tandem using 2 separate addition funnels and utilizing a Claisen adapter. The reaction mixture was stirred for 30 minutes in the ice bath and then for 5 hours at room temperature. The flask was cooled in an ice bath and the peroxide was carefully quenched with manganese dioxide. After filtration of the mixture over a small bed of silica gel followed by rinsing of the silica gel with ethyl acetate, the mixture was washed with brine. The organics were then dried over anhydrous magnesium sulfate, filtered, and evaporated. The resulting oil was treated with pentane to precipitate an off white solid after solvent evaporation yielding 2 g (56%) of compound (4). $^1$H NMR indicated 20% starting material in the mixture, which was easily removed in the next step (treatment with TFA). The $^1$H NMR of the product was consistent with that reported in the literature (*Synthesis* 1998, 775).

D. Preparation of 4-amino-5,5-dimethoxy-7-oxabicyclo[4.1.0]hept-3-en-2-one (5)

A solution of compound 4 (300 mg, 1.1 mmol) in anhydrous dichloromethane (6 mL) was stirred in an ice bath under an inert nitrogen atmosphere. To this solution was added trifluoroacetic acid (1.5 mL) drop-wise and the solution was brought to room temperature, stirring 3 hours. After judging complete by thin layer chromatography, the solvents were evaporated and the residue was dissolved in ethyl acetate. Solid sodium bicarbonate (2 g) was carefully added and the solution was stirred 10 minutes. The salt was filtered and rinsed with ethyl acetate before evaporation of the solvent. The crude compound was purified over silica gel using a gradient of ethyl acetate (0 to 100%) in heptane. The product eluted in 100% ethyl acetate giving 178 mg (91%) of compound (5). The $^1$H NMR of the product was consistent with that reported in the literature (*Synthesis* 1998, 775).

E. Preparation of N-(2,2-dimethoxy-5-oxo-7-oxabicyclo[4.1.0]hept-3-en-3-yl)-2-hydroxynicotinamide (6a)

A mixture 2-hydroxynicotinic acid (112 mg, 0.81 mmol) and thionyl chloride (650 mL, 8.9 mmol) was heated to reflux for 30 minutes. After cooling to room temperature, the excess thionyl chloride was removed under vacuum and the resulting acid chloride stored under an inert nitrogen atmosphere. Separately, a flask containing the amine 5 (100 mg, 0.54 mmol) in anhydrous tetrahydrofuran (4 mL) was cooled to −78° C. under and inert nitrogen atmosphere before the drop-wise addition of lithium tert-butoxide (in 1M tetrahydrofuran, 540 mL, 0.54 mmol). This solution was stirred for 30 minutes before the drop-wise addition of the crude 2-hydroxynicotinoyl chloride (in 1 mL tetrahydrofuran). The reaction mixture was stirred at −78° C. for 30 minutes and then warmed to room temperature and stirred for an hour. Liquid chromatography-mass spectra (LC-MS) indicated both desired and over-acylated products. The reaction mixture was then diluted with ethyl acetate, rinsed with saturated ammonium chloride, followed by brine, and the aqueous was back-extracted with ethyl acetate, followed by a brine wash. The combined organics were dried over anhydrous magnesium sulfate before filtration and solvent evaporation, affording 169 mg crude material. Chromatography with silica gel using a gradient of ethyl acetate (50 to 100%) in heptane afforded 56 mg of a mixture of product and starting material, 56 mg of a mixture of desired product and over-acylated product, and 31 mg of primarily over-acylated product (crude yield: 99%) The 56 mg mixture of desired/over-acylated material was dissolved in methanol (1.4 mL) and water (200 mL) before the addition of potassium carbonate (9 mg, ~1 equiv.). The reaction was stirred for 2 hours at room temperature before judging complete by thin layer chromatography. The solution was diluted with ethyl acetate and washed with brine before drying over anhydrous magnesium sulfate, filtration, and solvent evaporation to afford 50 mg compound 6a. The product structure was confirmed by $^1$H NMR. NMR (CDCl$_3$): δ12.10 (br.s, 1H), 10.60 (br.s, 1H), 8.62 (m, 1H), 7.55 (m, 1H), 7.25 (m, 1H), 6.60 (m, 1H), 3.85 (m, 1H), 3.70 (s, 3H), 3.50 (m, 1H), 3.40 (s, 3H) ppm.

F. Preparation of N-(2,5-dioxo-7-oxabicyclo[4.1.0]hept-3-en-3-yl)-2-hydroxynicotinamide (7a)

To a solution of 6a (50 mg, 0.16 mmol) in anhydrous dichloromethane (2 was slowly added trifluoroacetic acid (0.5 mL) at room temperature. After overnight stirring, LC-MS indicated 27% starting material remained. Additional trifluoroacetic acid (0.5 mL) was added and the reaction mixture was stirred an additional 24 hours, at which time it was judged complete. The solution was cooled in an ice bath and diluted with additional dichloromethane (10 mL) before the slow addition of saturated sodium bicarbonate solution until the stirring mixture was alkaline. The mixture was then partitioned and the organic solvents were removed and rinsed with brine. The aqueous layer was extracted twice with ethyl acetate and the organic layer was washed with brine. All organics were pooled and dried over anhydrous magnesium sulfate before filtration and solvent evaporation, giving 7a as a light-yellow solid (30 mg, 71%). LC-MS indicated 80% purity, and the material was used in the next step without further purification.

G. Preparation of (±)-2-hydroxy-N-(2-hydroxy-5-oxo-7-oxabicyclo[4.1.0]hept-3-en-3-yl)nicotinamide (8a)

To a solution of compound 7a (30 mg, 0.092 mmol, 80% purity) in methanol (4 mL) cooled to 0° C. under an inert nitrogen atmosphere was added sodium triacetoxyborohydride (30 mg, 0.142 mmol) in one portion. The solution was stirred at this temperature for 15 minutes before bringing to room temperature. After stirring an additional 45 minutes, the reaction was judged complete by TLC. The methanol was evaporated to approx. 2 mL volume and the flask was cooled in an ice bath for 10 minutes. The precipitate was then filtered and rinsed with methanol (2×3 mL). After drying under high vacuum, 10 mg (42% yield) of compound 8a as a pale yellow solid was isolated. The purity was 95% by HPLC (Restek Pinnacle II column, C18, 5μ, 250×4.6 mm; mobile phase: 5 minutes at 5% acetonitrile in water, then 5 to 100% acetonitrile in water over 20 min.; flow rate: 1.5 mL/min; detector: 316 nm (VWD). The product structure was confirmed by $^1$H NMR. NMR (DMSO-d$_6$): δ12.70 (br.s, 1H), 12.50 (br.s, 1H), 8.35 (m, 1H), 7.85 (m, 1H), 6.90 (m, 1H), 6.55 (m, 2H), 4.80 (m, 1H), 3.80 (m, 1H), 3.40 (m, 1H) ppm.

Example 2

(±)-2-hydroxy-N-(2-hydroxy-5-oxo-7-oxabicyclo[4.1.0]hept-3-en-3-yl)quinoline-3-carboxamide (8b)

Employing the method of Example 1, but using 2-hydroxyquinoline-3-carboxylic acid instead of 2-hydroxynicotinic acid in step E, 2-hydroxy-N-(2-hydroxy-5-oxo-7-oxabicyclo[4.1.0]hept-3-en-3-yl)quinoline-3-carboxamide was prepared.

A. Preparation of N-(2,2-dimethoxy-5-oxo-7-oxabicyclo[4.1.0]hept-3-en-3-yl)-2-hydroxyquinoline-3-carboxamide (6b)

In a dry round bottom flask charged with 2-hydroxyquinoline-3-carboxylic acid (528 mg, 2.8 mmol) was added thionyl chloride (4 mL, 57 mmol). The mixture was then heated to reflux for 20 minutes before rotary evaporation of the thionyl chloride. In a separate flask amine 5 (430 mg, 2.3 mmol) was dissolved in anhydrous tetrahydrofuran (17 mL) and cooled to −78° C. under an inert nitrogen atmosphere. To the cooled amine solution was slowly added lithium tert-butoxide (in 1 M tetrahydrofuran; 3 mL, 3 mmol) followed by stirring for 15 minutes. The acid chloride was then suspended in tetrahydrofuran (12 mL) and directly added to the cooled amine solution. The reaction mixture was stirred overnight, during which time it came to room temperature. The reaction was then diluted with ethyl acetate, washed with brine, dried over anhydrous magnesium sulfate, filtered and concentrated to afford 550 mg crude material that contained 10% of the O-aroylated product (as determined by LC-MS). The solid was stirred in 8/1 methanol/water (9 mL) containing 25 mg potassium carbonate for an hour after which it was diluted with ethyl acetate and washed with saturated sodium bicarbonate solution, and brine. The ethyl acetate was dried over anhydrous magnesium sulfate, filtered and concentrated give a solid containing a small amount of the ester. The product was then purified over a small plug of silica, eluting with 95/5 dichloromethane/ethyl acetate to give 530 mg of a pale yellow solid (64% yield). The product structure was confirmed by $^1$H NMR. NMR (CDCl$_3$): δ12.30 (br.s, 1H), 10.60 (br.s, 1H), 9.00 (m, 1H), 7.80 (m, 1H), 7.65 (m, 1H), 7.40 (m, 2H), 5.60 (m, 1H), 3.85 (m, 1H), 3.70 (s, 3H), 3.50 (m, 1H), 3.40 (s, 3H) ppm.

B. Preparation of N-(2,5-dioxo-7-oxabicyclo[4.1.0]hept-3-en-3-yl)-2-hydroxyquinoline-3-carboxamide (7b)

To a flask containing N-(2,2-dimethoxy-5-oxo-7-oxabicyclo[4.1.0]hept-3-en-3-yl)-2-hydroxyquinoline-3-carboxamide (65 mg, 0.18 mmol) was added trifluoroacetic acid (15 mL) in one portion. The solution was stirred 3 hours, after which the reaction was judged complete by LC-MS. The trifluoroacetic acid was removed in vacuo and the product dried with a stream of nitrogen to afford 57 mg (100%) of the title product that contained ca. 15% of a byproduct that was suggested to be the hydrolyzed product (at both amide and epoxide positions; M$^+$ 204). The solid was used in the next step without additional characterization or purification.

C. Preparation of (±)-2-hydroxy-N-(2-hydroxy-5-oxo-7-oxabicyclo[4.1.0]hept-3-en-3-yl)quinoline-3-carboxamide (8b)

The compound obtained above was dissolved in a 2/1 tetrahydrofuran/methanol mixture (36 mL) and cooled to 0° C. Sodium triacetoxyborohydride was then added in one portion and the reaction was brought to room temperature. After stiffing for 30 minutes, the reaction was complete as judged by LC-MS. The solvents were then evaporated and methanol (5 mL) was added. The mixture was briefly sonicated and cooled in an ice bath for 15 minutes. The solid was then filtered and rinsed with methanol (2×2 mL), collected, and dried under high vacuum to afford 18 mg (78%) of the product. The purity was 94% by HPLC (Restek Pinnacle II column, C18, 5µ, 150×4.6 mm; mobile phase: 5 minutes at 5% acetonitrile in water (0.1% TFA), then 5 to 100% acetonitrile in water (0.1% trifluoroacetic acid) over 20 min.; flow rate: 1.5 mL/min.; detector: 316 nm (VWD)). The product structure was confirmed by $^1$H NMR. NMR (DMSO-d$_6$): δ12.70 (br.s, 1H), 12.50 (br.s, 1H), 9.00 (m, 1H), 8.00 (m, 1H), 7.75 (m, 1H), 7.40 (m, 1H), 7.30 (m, 1H), 6.85 (m, 1H), 6.65 (m, 1H), 4.90 (m, 1H), 3.80 (m, 1H), 3.40 (m, 1H) ppm.

Example 3

(±)-3-hydroxy-N-(2-hydroxy-5-oxo-7-oxabicyclo[4.1.0]hept-3-en-3-yl)picolinamide $^1$H NMR. NMR (DMSO-d$_6$): δ 11.20 (br.s, 1H), 10.70 (br.s, 1H), 8.20 (m, 1H), 7.60 (m, 1H), 7.50 (m, 1H), 6.90 (m, 1H), 6.80 (m, 1H), 4.90 (m, 1H), 3.85 (m, 1H), 3.45 (m, 1H) ppm.

Example 4

(±)-4-hydroxy-N-(2-hydroxy-5-oxo-7-oxa-bicyclo[4.1.0]hept-3-en-3-yl)-nicotinamide $^1$H NMR. NMR (DMSO-d$_6$): δ 12.90 (br.s, 1H), 8.50 (m, 1H), 7.80 (m, 1H), 6.90 (m, 1H), 6.45 (m, 2H), 4.75 (m, 1H), 3.80 (m, 1H), 3.40 (m, 1H) ppm.

Example 5

(±)-6-chloro-4-hydroxy-quinoline-3-carboxylic acid-(2-hydroxy-5-oxo-7-oxa-bicyclo[4.1.0]hept-3-en-3-yl)-amide $^1$H NMR. NMR (DMSO-d$_6$): δ13.1 (br.s, 1H), 12.50 (br.s, 1H), 8.90 (m, 1H), 8.20 (m, 1H), 7.80 (m, 1H), 7.75 (m, 1H), 6.90 (m, 1H), 6.60 (m, 1H), 4.80 (m, 1H), 3.80 (m, 1H), 3.40 (m, 1H) ppm.

Example 6

(±)-4-hydroxy-8-trifluoromethyl-quinoline-3-carboxylic acid-(2-hydroxy-5-oxo-7-oxa-bicyclo[4.1.0]hept-3-en-3-yl)-amide $^1$H NMR. NMR (DMSO-d$_6$): δ 12.30 (br.s, 1H), 8.75 (m, 1H), 8.60 (m, 1H), 8.25 (m, 1H), 7.70 (m, 1H), 6.90 (m, 1H), 6.60 (m, 1H), 4.80 (m, 1H), 3.80 (m, 1H), 3.40 (m, 1H) ppm.

Example 7

(±)-5-chloro-2-hydroxy-N-(2-hydroxy-5-oxo-7-oxabicyclo[4.1.0]hept-3-en-3-yl)-nicotinamide $^1$H NMR. NMR (DMSO-d$_6$): δ 13.10 (br.s, 1H), 12.65 (br.s, 1H), 8.25 (m, 1H), 8.20 (m, 1H), 8.05 (m, 1H), 6.90 (m, 1H), 6.55 (m, 1H), 4.80 (m, 1H), 3.80 (m, 1H), 3.40 (m, 1H) ppm.

Example 8

(±)-4-hydroxy-2-phenylpyrimidine-5-carboxylic acid (2-hydroxy-5-oxo-7-oxa-bicyclo[4.1.0]hept-3-en-3-yl)-amide $^1$H NMR. NMR (DMSO-d$_6$): δ 13.70 (br.s, 1H), 12.00 (br.s, 1H), 8.75 (m, 1H), 8.20 (m, 2H), 7.50 (m, 3H), 6.90 (m, 1H), 6.60 (m, 1H), 4.80 (m, 1H), 3.80 (m, 1H), 3.40 (m, 1H) ppm.

Example 9

(±)-3-hydroxy-quinoxaline-2-carboxylic acid (2-hydroxy-5-oxo-7-oxa-bicyclo[4.1.0]hept-3-en-3-yl)-amide $^1$H NMR. NMR (DMSO-d$_6$): δ 13.00 (br.s, 1H), 7.90 (m, 1H), 7.70 (m, 1H), 7.40 (m, 2H), 6.90 (m, 1H), 6.60 (m, 1H), 4.80 (m, 1H), 3.80 (m, 1H), 3.40 (m, 1H) ppm.

Example 10

(±)-2-hydroxy-N-(2-hydroxy-5-oxo-7-oxa-bicyclo[4.1.0]hept-3-en-3-yl)-6-methyl-nicotinamide $^1$H NMR. NMR (DMSO-d$_6$): δ 12.60 (br.s, 1H), 12.20 (s, 1H), 8.25 (m, 1H), 6.90 (m, 1H), 6.60 (m, 1H), 6.40 (m, 1H), 4.80 (m, 1H), 3.80 (m, 1H), 3.40 (m, 1H), 2.35 (s, 3H) ppm.

Example 11

(±)-4-hydroxy-2-piperidin-1-yl-pyrimidine-5-carboxylic acid (2-hydroxy-5-oxo-7-oxa-bicyclo[4.1.0]hept-3-en-3-yl)-amide $^1$H NMR. NMR (DMSO-$d_6$): 8.50 (m, 1H), 6.80 (m, 1H), 6.50 (m, 1H), 4.75 (m, 1H), 3.85 (m, 1H), 3.80 (m, 4H), 3.40 (m, 1H), 1.6 (m, 6H) ppm.

Example 12

(±)-3-hydroxy-N-(2-hydroxy-5-oxo-7-oxabicyclo[4.1.0]hept-3-en-3-yl)picolinamide, mesylate $^1$H NMR. NMR (DMSO-$d_6$): δ 10.60 (br.s, 1H), 8.30 (m, 1H), 7.60 (m, 1H), 7.50 (m, 1H), 6.90 (m, 1H), 5.00 (m, 1H), 3.80 (m, 1H), 3.40 (m, 1H), 3.20 (m, 1H), 2.20 (s, 3H) ppm.

Example 13

(±)-3-hydroxy-N-(2-hydroxy-5-oxo-7-oxabicyclo[4.1.0]hept-3-en-3-yl)picolinamide trifluoroacetate $^1$H NMR. NMR (DMSO-$d_6$): δ 11.10 (br.s, 1H), 10.60 (br.s), 8.30 (m, 1H), 7.60 (m, 1H), 7.50 (m, 1H), 6.90 (m, 1H), 6.80 (m, 1H), 3.80 (m, 1H), 3.40 (m, 1H) ppm.

Example 14

(±)-3-hydroxy-N-(2-hydroxy-5-oxo-7-oxabicyclo[4.1.0]hept-3-en-3-yl)picolinamide tosylate $^1$H NMR. NMR (DMSO-$d_6$): δ 10.60 (br.s, 1H), 8.20 (m, 1H), 7.60 (m, 1H), 7.50 (m, 1H), 7.40 (m, 2H), 7.10 (m, 2H), 6.80 (m, 1H), 4.80 (m, 1H), 3.80 (m, 1H), 3.40 (m, 1H), 2.2 (s, 3H) ppm.

Example 15

(±)-3-hydroxy-quinoline-2-carboxylic acid-(2-hydroxy-5-oxo-7-oxa-bicyclo[4.1.0]hept-3-en-3-yl)-amide $^1$H NMR. NMR (DMSO-$d_6$): δ 10.90 (br.s, 1H), 10.80 (br.s, 1H), 7.90 (m, 3H), 7.60 (m, 2H), 6.90 (m, 1H), 6.80 (m, 1H), 4.90 (m, 1H), 3.80 (m, 1H), 3.40 (m, 1H) ppm.

Example 16

(±)-N-(2-hydroxy-5-oxo-7-oxa-bicyclo[4.1.0]hept-3-en-3-yl)-2-methoxy-nicotinamide $^1$H NMR. NMR (DMSO-$d_6$): δ 10.70 (br.s, 1H), 8.40 (m, 1H), 8.35 (m, 1H), 7.20 (m, 1H), 6.90 (m, 1H), 6.80 (m, 1H), 4.80 (m, 1H), 4.05 (s, 3H), 3.80 (m, 1H), 3.40 (m, 1H) ppm.

Example 17

(±)-3-hydroxy-quinoline-2-carboxylic acid-(2-hydroxy-5-oxo-7-oxa-bicyclo[4.1.0]hept-3-en-3-yl)-amide mesylate $^1$H NMR. NMR (DMSO-$d_6$): δ 10.90 (br.s, 1H), 10.80 (br.s, 1H), 7.90 (m, 3H), 7.60 (m, 2H), 6.90 (m, 1H), 4.80 (m, 1H), 3.80 (m, 1H), 3.40 (m, 1H), 2.30 (s, 3H) ppm.

Example 18

(±)-3-hydroxy-quinoline-2-carboxylic acid-(2-hydroxy-5-oxo-7-oxa-bicyclo[4.1.0]hept-3-3-yl)-amide trifluoroacetate $^1$H NMR. NMR (DMSO-$d_6$): δ 10.90 (br.s, 1H), 10.80 (br.s, 1H), 7.90 (m, 3H), 7.60 (m, 2H), 6.90 (m, 1H), 6.80 (m, 1H) 4.90 (m, 1H), 3.90 (m, 1H), 3.50 (m, 1H) ppm.

Example 19

(±)-3-hydroxy-quinoline-2-carboxylic acid-(2-hydroxy-5-oxo-7-oxa-bicyclo[4.1.0]hept-3-en-3-yl)-amide tosylate $^1$H NMR. NMR (DMSO-$d_6$): δ 10.90 (br.s, 1H), 10.80 (br.s, 1H), 7.90 (m, 3H), 7.60 (m, 2H), 7.40 (m, 2H), 7.1 (m, 2H), 6.80 (m, 1H) 4.90 (m, 1H), 3.90 (m, 1H), 3.50 (m, 1H), 2.2 (s, 3H) ppm.

Example 20

(±)-3-methoxy-pyridine-2-carboxylic acid (2-hydroxy-5-oxo-7-oxa-bicyclo[4.1.0]hept-3-en-3-yl)-amide $^1$H NMR. NMR (DMSO-$d_6$): δ 10.60 (br.s, 1H), 8.30 (m, 1H), 7.80 (m, 1H), 7.65 (m, 1H), 7.00 (m, 1H), 5.70 (m, 1H), 4.90 (m, 1H), 4.00 (s, 3H), 3.90 (m, 1H), 3.40 (m, 1H) ppm.

Example 21

(±)-N-(2-hydroxy-5-oxo-7-oxa-bicyclo[4.1.0]hept-3-en-3-yl)-2-methoxy-nicotinamide trifluoroacetate $^1$H NMR. NMR (DMSO-$d_6$): δ 10.70 (br.s, 1H), 8.40 (m, 1H), 8.35 (m, 1H), 7.20 (m, 1H), 6.90 (m, 1H), 6.80 (m, 1H), 4.80 (m, 1H), 4.05 (s, 3H), 3.80 (m, 1H), 3.40 (m, 1H) ppm.

Example 22

(±)-3-methoxy-pyridine-2-carboxylic acid (2-hydroxy-5-oxo-7-oxa-bicyclo[4.1.0]hept-3-en-3-yl)-amide trifluoroacetate $^1$H NMR. NR (DMSO-$d_6$): δ 10.40 (br.s, 1H), 8.30 (m, 1H), 7.80 (m, 1H), 7.65 (m, 1H), 6.80 (m, 1H), 4.90 (m, 1H), 3.90 (s, 3H), 3.80 (m, 1H), 3.40 (m, 1H) ppm.

Example 23

(±)-2-hydroxy-N-(2-hydroxy-5-oxo-7-oxa-bicyclo[4.1.0]hept-3-en-3-yl)-6-trifluoromethyl-nicotinamide $^1$H NMR. NMR (DMSO-$d_6$): δ 11.80 (br.s, 1H), 8.50 (m, 1H), 7.20 (m, 1H), 6.90 (m, 1H), 6.80 (m, 1H), 4.80 (m, 1H), 3.80 (m, 1H), 3.40 (m, 1H) ppm.

Example 24

(±)-4-hydroxy-2-methyl-pyrimidine-5-carboxylic acid (2-hydroxy-5-oxo-7-oxa-bicyclo[4.1.0]hept-3-en-3-yl)-amide $^1$H NMR. NMR (DMSO-$d_6$): δ 13.40 (br.s, 1H), 11.80 (br.s, 1H), 8.60 (s, 1H), 6.90 (m, 1H), 6.60 (m, 1H), 4.80 (m, 1H), 3.80 (m, 1H), 3.40 (m, 1H) ppm.

Example 25

(±)-2-methoxy-quinoline-3-carboxylic acid (2-hydroxy-5-oxo-7-oxa-bicyclo[4.1.0]hept-3-en-3-yl)-amide $^1$H NMR. NMR (DMSO-d$_6$): δ 10.80 (br.s, 1H), 9.00 (m, 1H), 8.10 (m, 1H), 7.80 (m, 2H), 7.50 (m, 1H), 6.90 (m, 2H), 4.90 (m, 1H), 4.20 (s, 3H), 3.90 (m, 1H), 3.40 (m, 1H) ppm.

Example 26

(±)-3-methoxy-pyrazine-2-carboxylic acid (2-hydroxy-5-oxo-7-oxa-bicyclo[4.1.0]hept-3-en-3-yl)-amide $^1$H NMR. NMR (DMSO-d$_6$): δ 10.30 (br.s, 1H), 8.60 (s, 1H), 8.35 (m, 1H), 6.80 (m, 1H), 6.70 (m, 1H), 4.80 (m, 1H), 4.00 (s, 3H), 3.80 (m, 1H), 3.40 (m, 1H) ppm.

Example 27

(±)-1-chloro-4-hydroxy-isoquinoline-3-carboxylic acid (2-hydroxy-5-oxo-7-oxa-bicyclo[4.1.0]hept-3-en-3-yl)-amide $^1$H NMR. NMR (DMSO-d$_6$): δ 12.30 (br.s, 1H), 10.30 (br.s, 1H), 8.40 (m, 2H), 8.10 (m, 2H), 6.90 (m, 1H), 6.80 (m, 1H), 4.80 (m, 1H), 3.80 (m, 1H), 3.40 (m, 1H) ppm.

Example 28

(±)-N-(2,5-dioxo-7-oxabicyclo[4.1.0]hept-3-en-3-yl)-2-hydroxyquinoline-3-carboxamide $^1$H NMR. NMR (DMSO-d$_6$): δ 12.60 (br.s, 1H), 10.30 (br.s, 1H), 9.00 (m, 1H), 8.00 (m, 1H), 7.70 (m, 1H), 7.5 (m, 2H), 7.30 (m, 1H), 4.20 (m, 1H), 3.90 (m, 1H) ppm.

Example 29

(±)-N-(2-hydroxy-5-oxo-7-oxabicyclo[4.1.0]hept-3-en-3-yl)-8-methoxyquinoline-7-carboxamide $^1$H NMR. NMR (DMSO-d$_6$): δ 11.10 (br.s, 1H), 9.10 (s, 1H), 8.50 (m, 1H), 8.05 (m, 1H), 7.70 (m, 1H), 6.90 (m, 1H), 6.80 (m, 1H), 4.90 (m, 1H), 4.35 (s, 3H), 3.80 (m, 1H), 3.40 (m, 1H) ppm.

Example 30

(±)-N-(2,5-Dioxo-7-oxa-bicyclo[4.1.0]hept-3-en-3-yl)-2-methoxy-nicotinamide $^1$H NMR. NMR (DMSO-d$_6$): δ 10.60 (br.s, 1H), 8.50 (m, 1H), 8.30 (m, 1H), 7.40 (m, 1H), 7.20 (m, 1H), 4.20 (m, 1H), 4.10 (s, 3H), 3.95 (m, 1H) ppm.

Example 31

(±)-N-(2-hydroxy-5-oxo-7-oxabicyclo[4.1.0]hept-3-en-3-yl)-3-methoxyquinoline-2-carboxamide $^1$H NMR. NMR (DMSO-d$_6$): δ 10.60 (br.s, 1H), 8.05 (s, 1H), 8.00 (m, 2H), 7.60 (m, 2H), 6.80 (m, 1H), 6.60 (m, 1H), 4.80 (m, 1H), 3.80 (m, 1H), 3.40 (m, 1H) ppm.

Example 32

(±)-N-(2,5-diose-7-oxabicyclo[4.1.0]hept-3-en-3-yl)-8-methoxyquinoline-7-carboxamide $^1$H NMR. NMR (DMSO-d$_6$): δ 11.20 (br.s, 1H), 9.00 (s, 1H), 8.50 (m, 1H), 8.10 (m, 1H), 7.90 (m, 1H), 7.70 (m, 1H), 7.40 (m, 1H), 4.40 (s, 3H), 4.20 (m, 1H), 4.00 (m, 1H) ppm.

Example 33

(±)-N-(2-hydroxy-5-oxo-7-oxabicyclo[4.1.0]hept-3-en-3-yl)-8-methoxyquinoline-7-carboxamide trifluoroacetate $^1$H NMR. NMR (DMSO-d$_6$): δ 11.20 (br.s, 1H), 9.00 (s, 1H), 8.50 (m, 1H), 8.10 (m, 1H), 7.90 (m, 1H), 7.70 (m, 1H), 7.00 (m, 1H), 4.90 (s, 3H), 3.90 (m, 1H) ppm.

Example 34

(±)-N-(2,5-dioxo-7-oxabicyclo[4.1.0]hept-3-en-3-yl)-3-hydroxyisonicotinamide $^1$H NMR. NMR (DMSO-d$_6$): δ 8.30 (s, 1H), 8.00 (m, 1H), 7.40 (m, 1H), 4.20 (s, 1H), 4.00 (m, 1H) ppm.

Example 35

(±)-N-(2,5-dioxo-7-oxabicyclo[4.1.0]hept-3-en-3-yl)-2-methoxyquinoline-3-carboxamide $^1$H NMR. NMR/DMS (1-d$_6$): δ 11.00 (br.s, 1H), 9.00 (s, 1H), 7.90 (m, 2H), 7.75 (m, 2H), 7.50 (m, 1H), 4.40 (s, 3H), 4.00 (s, 1H), 3.90 (m, 1H) ppm.

Example 36

(±)-2-hydroxy-N-(2-hydroxy-5-oxo-7-oxabicyclo[4.1.0]hept-3-en-3-yl)-6-methoxyquinoline-3-carboxamide $^1$H NMR. NMR (DMSO-d$_o$): δ12.50 (br.s, 1H), 8.90 (m, 1H), 7.50 (m, 1H), 7.40 (m, 2H), 6.90 (m, 1H), 6.60 (m, 1H), 4.90 (m, 1H), 3.80 (m, 4H), 3.40 (m, 1H) ppm.

Example 37

(±)-6-hydroxy-N-(2-hydroxy-5-oxo-7-oxabicyclo[4.1.0]hept 3-en-3-yl)benzo[d]oxazole-5-carboxamide Employing the method of Example 1, but using 6-hydroxy-benzo[d]oxazole-5-carboxylic acid instead of 2-hydroxynicotinic acid in step E, (±)-6-hydroxy-N-(2-hydroxy-5-oxo-7-oxabicyclo[4.1.0]hept-3-en-3-yl)benzo[d]oxazole-5-carboxamide may be prepared.

Example 38

(±)-6-hydroxy-N-(2-hydroxy-5-oxo-7-oxabicyclo[4.1.0]hept-3-en-3-yl)benzo[d]thiazole-5-carboxamide Employing the method of Example 1, but using 6-hydroxy-benzo[d]thiazole-5-carboxylic acid instead of 2-hydroxynicotinic acid in step E, (±)-6-hydroxy-N-(2-hydroxy-5-oxo-7- oxabicyclo[4.1.0]hept-3-en-3-yl)benzo[d]thiazole-5-carboxamide may be prepared.

Example 39

(±)-3-hydroxy-N-(2-hydroxy-5-oxo-7-oxabicyclo[4.1.0]hept-3-en-3-yl)piperidine-2-carboxamide Employing the method of Example 1, but using 3-hydroxypiperidine-2-carboxylic acid instead of 2-hydroxynicotinic acid in step E, (±)-3-hydroxy-N-(2-hydroxy-5-oxo-7-oxabicyclo[4.1.0]hept-3-en-3-yl)piperidine-2-carboxamide may be prepared.

Example 40

(±)-3-hydroxy-N-(2-hydroxy-5-oxo-7-oxabicyclo[4.1.0]hept-3-en-3-yl)pyrazine-2-carboxamide Employing the method of Example 1, but using 3-hydroxypyrazine-2-carboxylic acid instead of 2-hydroxynicotinic acid in step E, (±)-3-hydroxy-N-(2-hydroxy-5-oxo-7-oxabicyclo[4.1.0]hept-3-en-3-yl)pyrazine-2-carboxamide may be prepared.

Example 41

(±)-5-hydroxy-N-(2-hydroxy-5-oxo-7-oxabicyclo[4.1.0]hept-3-en-3-yl)pyrimidine-4-carboxamide Employing the method of Example 1, but using 5-hydroxypyrimidine-4-carboxylic acid instead of 2-hydroxynicotinic acid in step E, (±)-5-hydroxy-N-(2-hydroxy-5-oxo-7-oxabicyclo[4.1.0]hept-3-en-3-yl)pyrimidine-4-carboxamide may be prepared.

Example 42

(±)-2-hydroxy-N-(2-hydroxy-5-oxo-7-oxabicyclo[4.1.0]hept-3-en-3-yl)-1,8-naphthyridine-3-carboxamide Employing the method of Example 1, but using 2-hydroxy-1,8-naphthyridine-3-carboxylic acid instead of 2-hydroxynicotinic acid in step E, (±)-2-hydroxy-N-(2-hydroxy-5-oxo-7-oxabicyclo[4.1.0]hept-3-en-3-yl)-1,8-naphthyridine-3-carboxamide may be prepared.

Example 43

(±)-7-hydroxy-N-(2-hydroxy-5-oxo-7-oxabicyclo[4.1.0]hept-3-en-3-yl)pyrido[2,3-d]pyrimidine-6-carboxamide Employing the method of Example 1, but using 7-hydroxypyrido[2,3-d]pyrimidine-6-carboxylic acid instead of 2-hydroxynicotinic acid in step E, (±)-7-hydroxy-N-(2-hydroxy-5-oxo-7-oxabicyclo[4.1.0]hept-3-en-3-yl)pyrido[2,3-d]pyrimidine-6-carboxamide may be prepared.

Example 44

(±)-4-hydroxy-N-(2-hydroxy-5-oxo-7-oxabicyclo[4.1.0]hept-3-en-3-yl)pyridazine-3-carboxamide Employing the method of Example 1, but using 4-hydroxy-pyridazine-3-carboxylic acid instead of 2-hydroxynicotinic acid in step E, (±)-4-hydroxy-N-(2-hydroxy-5-oxo-7-oxabicyclo[4.1.0]hept-3-en-3-yl)pyridazine-3-carboxamide may be prepared.

Example 45

(±)-4-hydroxy-N-(2-hydroxy-5-oxo-7-oxabieyclo[4.1.0]hept-3-en-3-yl)-1H-pyrazole-3-carboxamide Employing the method of Example 1, but using 4-hydroxy-1H-pyrazole-3-carboxylic acid instead of 2-hydroxynicotinic acid in step E, (±)-4-hydroxy-N-(2-hydroxy-5-oxo-7-oxabicyclo[4.1.0]hept-3-en-3-yl)-1H-pyrazole-3-carboxamide may be prepared.

Example 46

4-hydroxy-N-(2-hydroxy-5-oxo-7-oxabicyclo[4.1.0]hept-3-en-3-yl)furan-3-carboxamide Employing the method of Example 1, but using 4-hydroxyfuran-3-carboxylic acid instead of 2-hydroxynicotinic acid in step E, 4-hydroxy-N-(2-hydroxy-5-oxo-7-oxabicyclo[4.1.0]hept-3-en-3-yl)furan-3-carboxamide may be prepared.

Example 47

(±)-4-hydroxy-N-(2-hydroxy-5-oxo-7-oxabicyclo[4.1.0]hept-3-en-3-yl)thiophene-3-carboxamide Employing the method of Example 1, but using 4-hydroxythiophene-3-carboxylic acid instead of 2-hydroxynicotinic acid in step E, (±)-4-hydroxy-N-(2-hydroxy-5-oxo-7-oxabicyclo[4.1.0]hept-3-en-3-yl)thiophene-3-carboxamide may be prepared.

Example 48

(±)-3-hydroxy-N-(2-hydroxy-5-oxo-7-oxabicyclo[4.1.0]hept-3-en-3-yl)isothiazole-4-carboxamide Employing the method of Example 1, but using 3-hydroxyisothiazole-4-carboxylic acid instead of 2-hydroxynicotinic acid in step E, (±)-3-hydroxy-N-(2-hydroxy-5-oxo-7-oxabicyclo[4.1.0]hept-3-en-3-yl)isothiazole-4-carboxamide may be prepared.

Example 49

(±)-3-hydroxy-N-(2-hydroxy-5-oxo-7-oxabicyclo[4.1.0]hept-3-en-3-yl)isoxazole-4-carboxamide Employing the method of Example 1, but using 3-hydroxyisoxazole-4-carboxylic acid instead of 2-hydroxynicotinic acid in step E, (±)-3-hydroxy-N-(2-hydroxy-5-oxo-7-oxabicyclo[4.1.0]hept-3-en-3-yl)isoxazole-4-carboxamide may be prepared.

Example 50

(±)-6-hydroxy-N-(2-hydroxy-5-oxo-7-oxabicyclo[4.1.0]hept-3-en-3-yl)-1H-indole-5-carboxamide Employing the method of Example 1, but using 6-hydroxy-1H-indole-5-carboxylic acid instead of 2-hydroxynicotinic acid in step E, (±)-6-hydroxy-N-(2-hydroxy-5-oxo-7-oxabicyclo[4.1.0]hept-3-en-3-yl)-1H-indole-5-carboxamide may be prepared.

Example 51

(±)-6-hydroxy-N-(2-hydroxy-5-oxo-7-oxabicyclo[4.1.0]hept-3-en-3-yl)-1H-benzo[d]imidazole-5-carboxamide Employing the method of Example 1, but using 6-hydroxy-1H-benzo[d]imidazole-5-carboxylic acid instead of 2-hydroxynicotinic acid in step E, (±)-6-hydroxy-N-(2-hydroxy-5-oxo-7-oxabicyclo[4.1.0]hept-3-en-3-yl)-1H-benzo[d]imidazole-5-carboxamide may be prepared.

Example 52

(±)-2-hydroxy-N-(2-hydroxy-5-oxo-7-oxabicyclo[4.1.0]hept-3-en-3-yl)morpholine-3-carboxamide Employing the method of Example 1, but using 2-hydroxymorpholine-3-carboxylic acid instead of 2-hydroxynicotinic acid in step E, (±)-2-hydroxy-N-(2-hydroxy-5-oxo-7-oxabicyclo[4.1.0]hept-3-en-3-yl)morpholine-3-carboxamide may be prepared.

Inhibition of NF-κB in cells by the compound of Example 1. Two reporter cell assays were used to determine the ability of the compound of Example 1 to inhibit NE-KB driven transcription. The first assay was a 293-cell based assay with a stably integrated pNF-κB-luc reporter plasmid containing 3 NF-κB promoter elements. The second assay was a 293-cell based assay with a stably integrated pTRH1-NF-κB-dscGFP reporter containing 4 NF-κB promoter elements. Cells were treated with 0, 0.2, 1, 10, 20 and 40 µM of the compound of Example 1 for 2 hours then were induced with 20 ng/ml TNF-α for 18 hours. Following the induction, luminescence or fluorescence was quantified using a Beckman-Coulter 2300 plate reader. FIGS. 1A and B shows the dose response curve generated from the luminescence and fluorescence data respectively. The compound of Example 1 was observed to inhibit the expression of the luciferase gene in a dose dependent manner with a median $IC_{50}$ (Inhibitory Concentration of 50%) of 16.2±1.1 µM. The compound of Example 1 also inhibited the expression of the Green fluorescent protein gene in a dose dependent manner with a median $IC_{50}$ of 6.2±0.5 µM. These values represent the median value generated from three independent experiments±the standard error. As a control, 0.5% DMSO treated and untreated cells were compared to verify that the Example 1 carrier had no effect on the expression of luciferase or in the readout of the assay. There was a slight decrease in the output from the assay in the DMSO treated population although it was not statistically significant. As a result of the controls, the decrease in activity in the drug treated samples was compared to the DMSO control sample.

Figure 2:
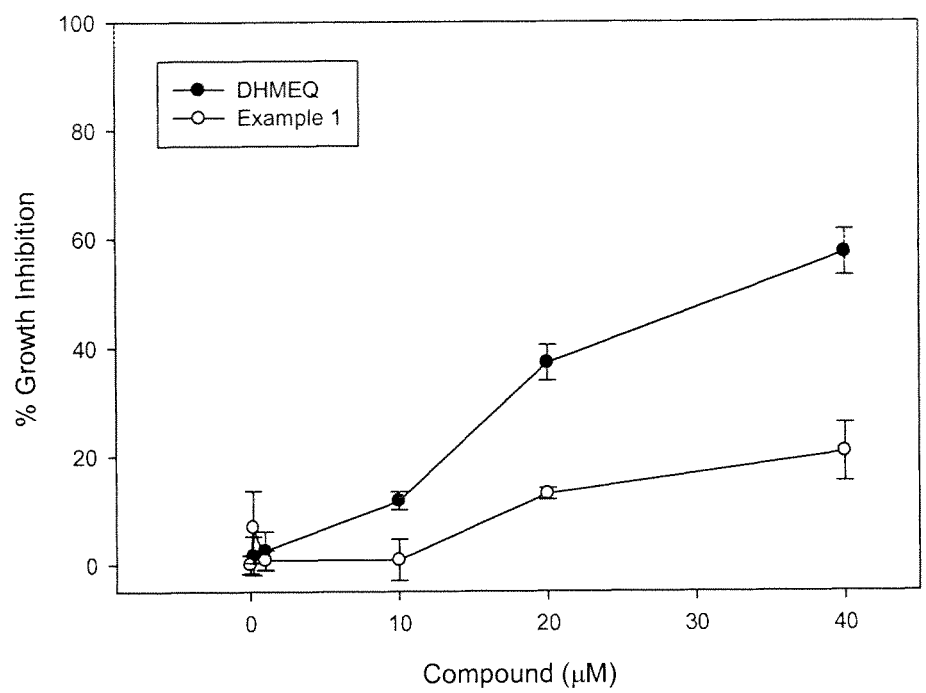
FIG. 2 shows the compound of Example 1 has little cytotoxic effect to hPBMCs. Human peripheral blood mononuclear cells (hPBMCs) were treated with example 1 or DHMEQ and the percentage of viable cells was assessed 24 hours post drug treatment. The graph represents the mean±the standard deviation of three replicate experiments.

The cytotoxicity profile of the compound of Example 1. The cytotoxicity of the compound of Example 1 was determined for human peripheral blood mononuclear cells (hPBMCs). See FIG. 2. As with the activity assay, the hPBMCs were treated with 0, 0.2, 1, 10, 20 and 40 µM of the compound of Example 1 for 2 hours, and then induced with 20 ng/ml TNF-α for 48 hours. The number of viable cells was determined using CellTiter-Glo luminescent cell viability assay (Promega (cat #G7573)). A representative experiment is shown in FIG. 2. As the graph shows, there was little detectable toxicity to these cells with the compound of Example 1 up to the 40 µM tested. In contrast, DHMEQ exhibited inhibition of cell growth of greater than 60% at 40 µM. Cells treated with 0.5% DMSO showed no detectable cytotoxic effects as compared to untreated hPBMCs. The selectivity index (the ratio of cytotoxicity $CC_{50}$ to inhibitory $IC_{50}$) is assigned to the compound of Example 1. Based on the results obtained in the inhibition and toxicity experiments described above, the compound of Example 1 exhibited greater selectivity (i.e., greater activity and lower cytotoxicity) compared to DHMEQ.

Figure 3:
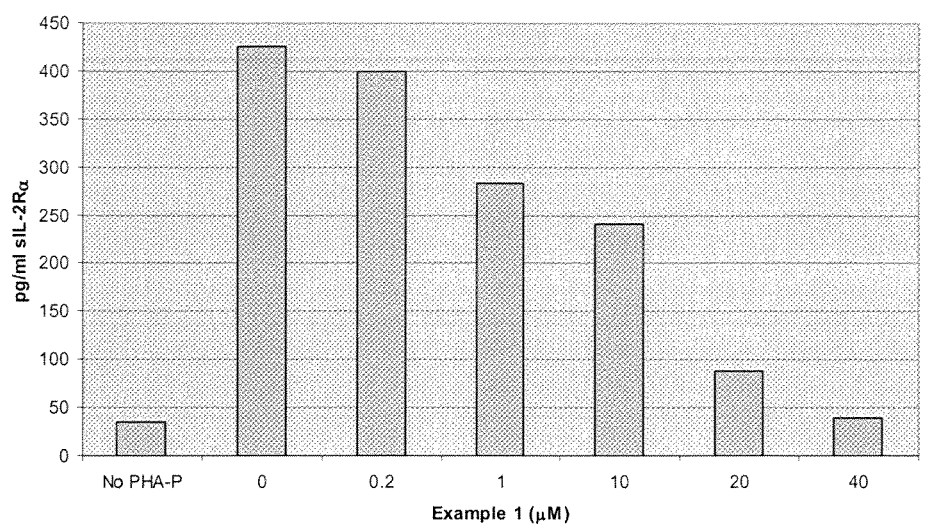
FIG. 3 shows the effects of the compound of Example 1 on the NF-κB dependent expression of soluble IL-2Rα, an NF-κB regulated cytokine, in hPBNICs. The graph is the mean of 2 independent experiments.

Soluble IL-2Rα is transcriptionally regulated by NF-κB. FIG. 3 demonstrates that serum levels of sIL-2Rα can be influenced by Example 1 treated cells. Human PBMCs were treated with 0, 0.2, 1, 10, 20 and 40 µM of the compound of Example 1 concurrent with PHA-P activation. The cells were cultured for an additional three days and media was harvested for marker assessment. FIG. 3 shows that sIL-2Rα was significantly induced by PHA-P activation. Further, the graph clearly demonstrates that sIL-2Rα was affected by the addition of the compound of Example 1 in a dose dependent manner, with 10 µM of the compound of Example 1 producing a statistically significant affect.

Inhibition of IL-6 and IL-8 Secretion by the compound of Example 1. Over the past few years, extensive studies on breast cancer have led to the recognition that overexpression of HER2, estrogen receptor (ER), and mutation of genes including p53, BRCA1, and BRCA2 play important roles in the development and progression of breast cancer via induction of multiple angiogenic, proapoptotic regulators, including nuclear factor κB. NF-κB is often constitutively activated in breast carcinomas, bladder carcinomas, prostate carcinomas, and melanomas. Numerous studies have shown that constitutive activation of NF-κB contributes to the progression of hormone-independent growth of breast cancer cell lines.

Figure 4:
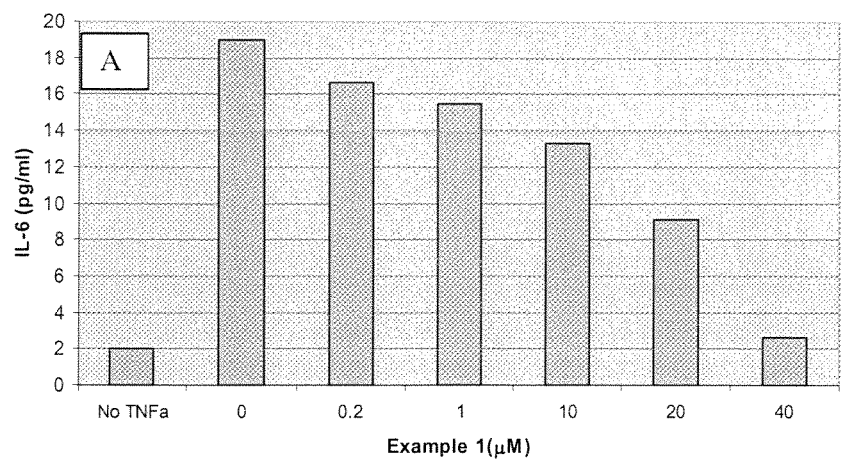
FIG. 4 shows the ability of the compound of Example 1 to inhibit the secretion of inflammatory cytokines, IL-6 (A) and IL-8 (B), in breast carcinoma cells in a dose dependent manner. Specifically, A and B show the effects of the compound of Example 1 on IL-6 and IL-8 secretion from MDA-MB-231 cells stimulated by 20 ng/mL TNF-α. The cells were treated with the indicated concentrations of the compound of Example 1 for 2 hours, and then TNF-α was added and incubation continued for 4 hours.
Figure 4:
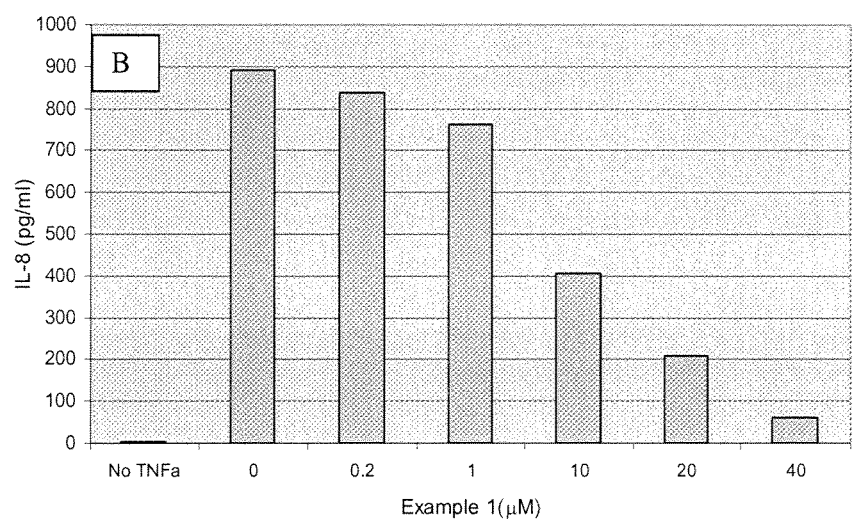

The NF-κB signaling pathway is constitutively activated in MDA-MB-231 cells which have been shown to secrete IL-6 and IL-8 constitutively, while the addition of TNF-α further accelerates this secretion (see FIGS. 4 A and B). The compound of Example 1 was observed to inhibit the constitutive IL-6 and IL-8 secretion from MDA-MB-231 in a dose-dependent manner. Even when cells were stimulated with TNF-α (20 ng/mL), 20 µM of the compound of Example 1 completely inhibited the IL-6 and Il-8 secretion from these cells (FIGS. 4A and B).

Macrophages play an important role in immune reactions, allergy, and inflammation. Excess macrophage activation may also enhance solid tumors, diabetes mellitus, and neural disorders such as Alzheimer's and Parkinson's diseases. Therefore, inhibition of excess macrophage activities should be useful as chemotherapy for these diseases. For cell culture studies, the mouse cell line RAW264.7 is often used as a model of macrophages. In response to microbes and their products such as lipopolysaccharide (LPS), macrophages secrete various inflammatory cytokines including interleukin (IL)-1, IL-2, IL-6, IL-8, IL-10, IL-12, and tumor necrosis factor (TNF)-α through the activation of nuclear factor NF-κB, as well as express NF-κB-dependent inducible NO synthase (iNOS) and cyclooxygenase-2 (COX-2). NF-κB is activated by extracellular signals mainly through the various Toll-like receptors in macrophages. Detection and response to microbial infections by the immune system depend on a family of pattern recognition receptors called Toll-like receptors (TLRs). These receptors have been evolutionally conserved to recognize pathogen-associated molecular patterns (PAMPs), including molecules from Gram-positive and -negative bacteria, DNA and RNA viruses, fungi, and protozoa; and they show considerable target specificity. TLR4 is crucial for the effective host cell responses to LPS of Gram-negative bacteria.

LPS stimulation induces the expression of COX-2 the enzyme responsible for prostaglandin E2. Pretreatment with the compound of Example 1 resulted in strong inhibition of the expression at 6 to 12 h. This decrease in LPS-induced COX-2 expression was dose dependent as shown by the decrease in downstream $PGE_2$ synthesis as shown in FIG. 5A.

Figure 5:
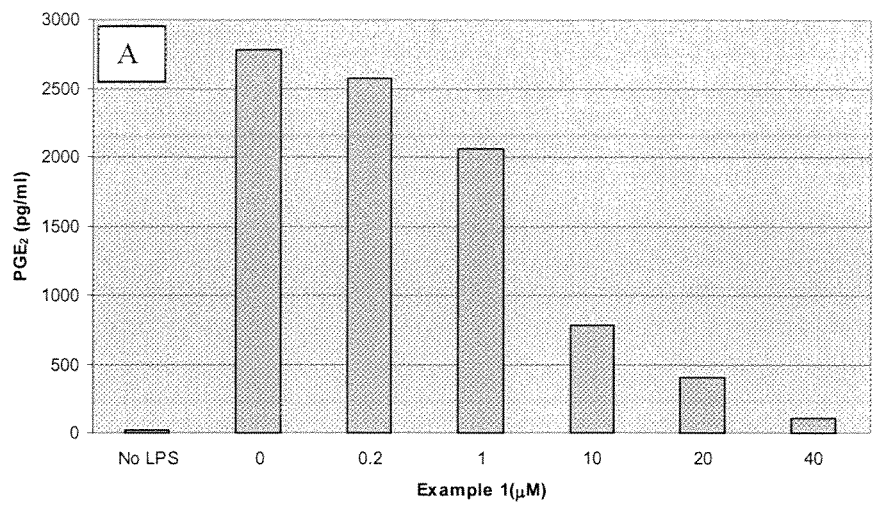
FIG. 5 shows the ability of the compound of Example 1 to inhibit the secretion of inflammatory cytokines, IL-6 and $PGE_2$, in LPS stimulated mouse macrophage cells in a dose dependent manner. Specifically, A and B show the effects of the compound of Example 1 on soluble $PGE_2$ and Il-6 secretion from RAW264.7 cells stimulated by 1 μg/mL of LPS. The cells were treated with the indicated concentrations of the compound of Example 1 for 2 hours, and then LPS was added and incubation continued for 4 hours.
Figure 5:
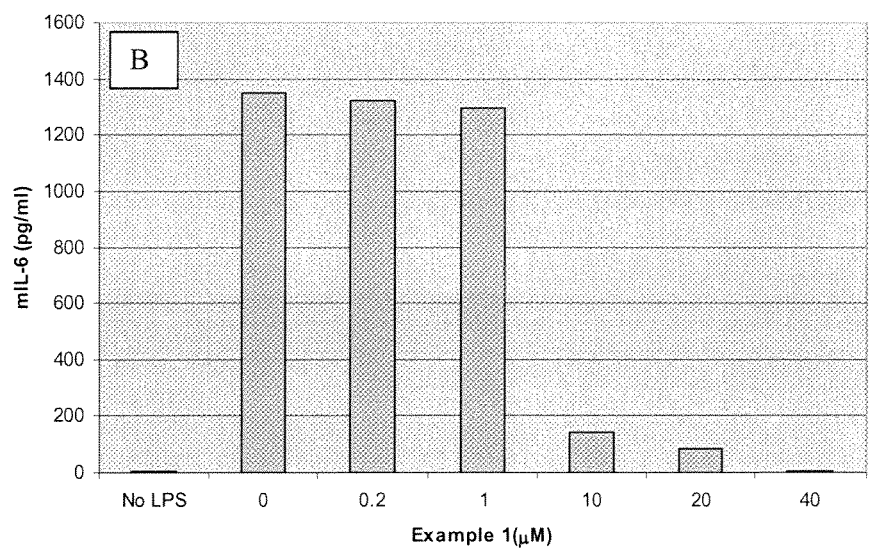

The inflammatory cytokine IL-6 was inhibited in a dose dependent manor by the compound of Example 1 as shown in FIG. 5B. This inhibition is consistent with the inhibition of IL-6 in MDA-MB-231 breast carcinoma cell line.

Figure 6:
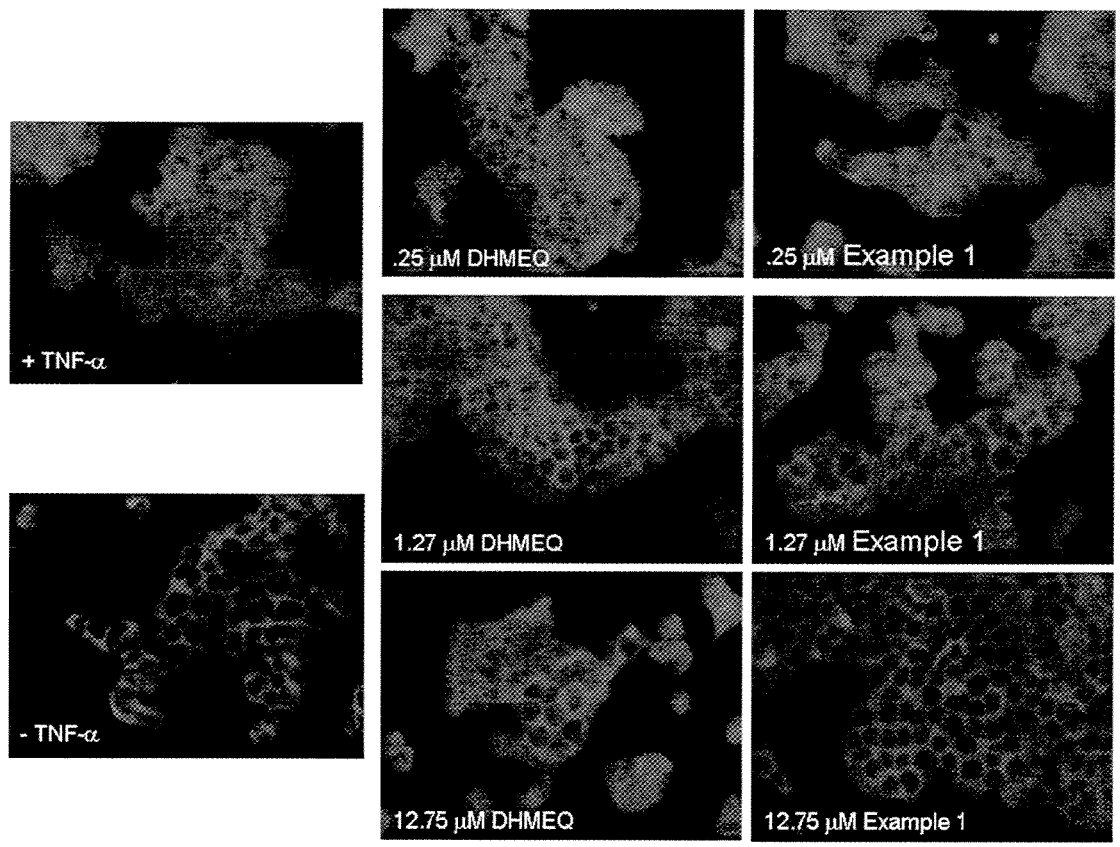
FIG. 6 shows the ability of the compound of Example 1 to block translocation of RelA/p65 from cytoplasm to nuclei in a dose dependent manner. Specifically, the compound of Example 1 causes the accumulation of activated RelA/p65 in the cytoplasm of cells. Hek293 cells were treated with DHMEQ or the compound of Example 1 (as indicated) with TNFα (20 ng/ml) for 30 minutes. After incubation, the cells were immunostained with anti-p65 antibody (C-20) antibody (Santa Cruz Biotechnology, Santa Cruz, Calif.) and nuclei were counterstained with Dapi. Images were captured using an AE31 inverted microscope with epifluorescence illuminator (Motic, Xiamen, China) and a ProgRes C3 camera (JENOPTIK, Jena, Germany). Individual images of p65 and corresponding nuclei were merged for final figure. Control treated cells (DMSO only) show nuclear accumulation of p65 upon TNFα stimulation. Nuclear accumulation of p65 induced by TNFα was significantly blocked by the compound of Example 1 at 1 to 12 μM whereas DHMEQ required higher concentration to achieve the same effect.

Immunostaining of RelA/p65. The compound of Example 1 causes the accumulation of activated RelA/p65 in the cytoplasm of cells. Hek293 cells were treated with DHMEQ or the compound of Example 1 (as indicated) with TNFα (20 ng/ml) for 30 minutes. After incubation, cells were immunostained with anti-p65 antibody (C-20) antibody (Santa Cruz Biotechnology, Santa Cruz, Calif.) and nuclei were counterstained with Dapi. Images were captured using an AE31 inverted microscope with epifluorescence illuminator (Motic, Xiamen, China) and a ProgRes C3 camera (JENOPTIK, Jena, Germany). Individual images of p65 and corresponding nuclei were merged for final figure. Control treated cells (DMSO only) exhibited nuclear accumulation of p65 upon TNFα stimulation. Nuclear accumulation of p65 induced by TNFα was significantly blocked by the compound of Example 1 at 1 to 12 μM whereas DHMEQ required a higher concentration to achieve the same effect. See FIG. 6.

Figure 7:
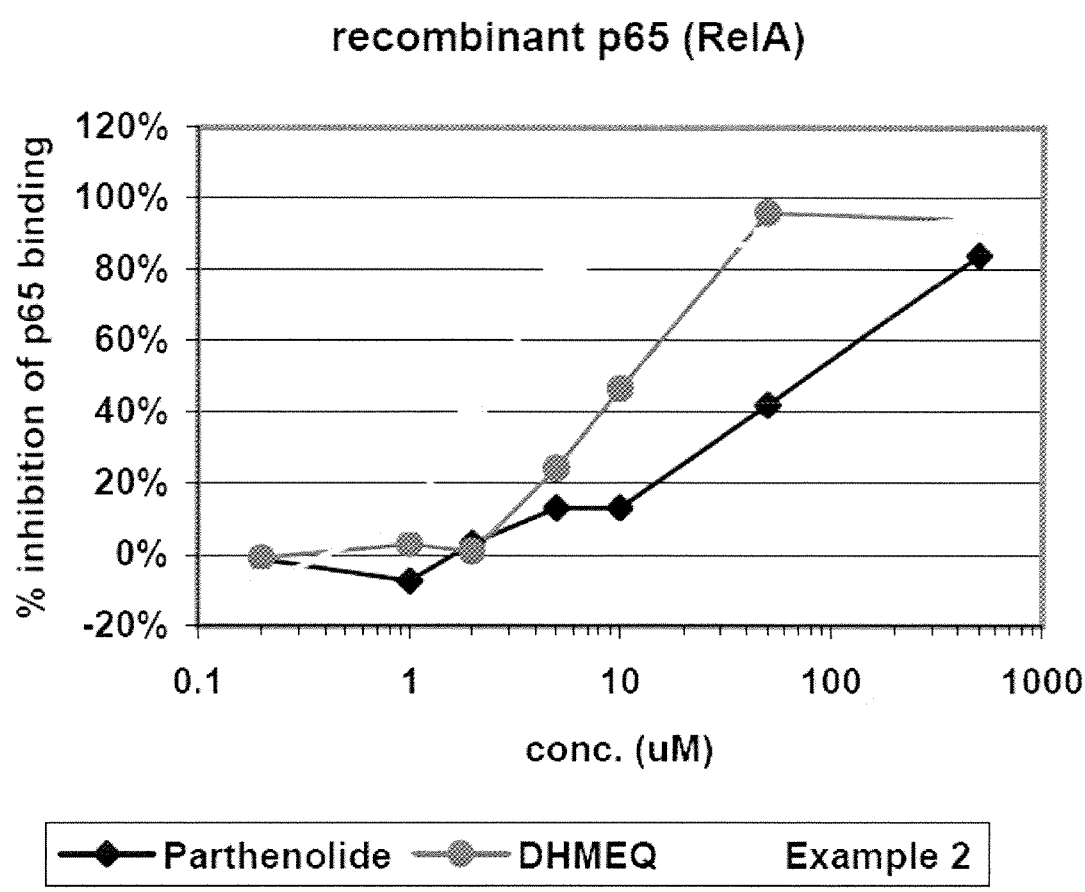
FIG. 7 shows that the compound of Example 2 inhibits p65 (RelA) binding to DNA in the canonical pathway more potently than DHMEQ and parthenolide.
Figure 8:
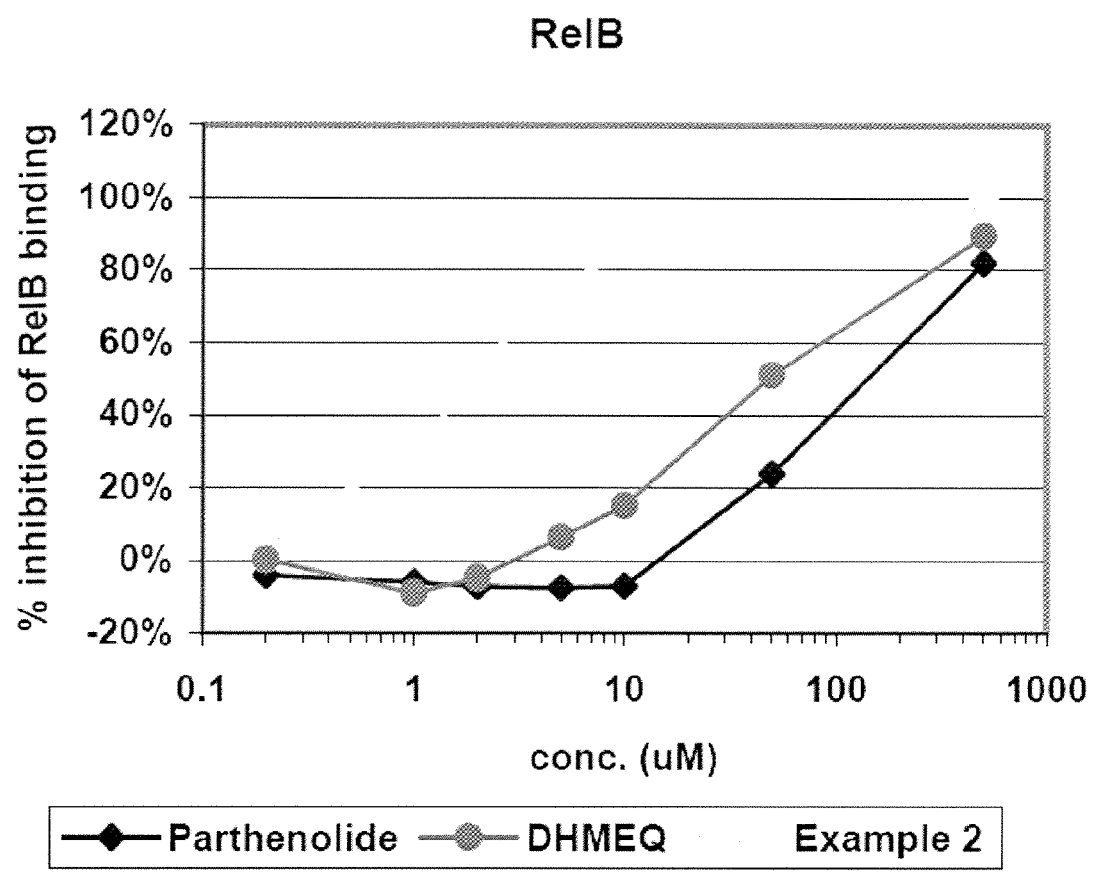
FIG. 8 shows that the compound of Example 2 inhibits RelB binding to DNA in the non-canonical pathway ($IC_{50}$~2 uM), while DHMEQ and parthenolide do not ($IC_{50}$>20 uM).

TransAM NF-κB Family DNA Binding ELISA: The binding activity of NF-κB heterodimer or homodimer subunits from activated nuclear extracts or purified recombinant NF-κB proteins exposed to the drug compounds was evaluated using the TransAM NF-κB Family binding ELISA (Active Motif). 3-5 μg of nuclear extracts from TNFα activated Hela or Raji cells (Active Motif) or 20 ng of purified recombinant proteins (p65 and p50 from Active Motif, p52 from Santa Cruz) were incubated for 1 hour at room temperature with 20 μL drug compounds diluted in Complete Lysis buffer without DTT. Treated samples were then transferred to 30 μL Complete Binding Buffer (with DTT) in microplate wells pre-coated with the NF-κB consensus oligonucleotide. Controls included non-specific binding (NSB) wells containing lysis buffer without any extract or recombinant protein (for background), nuclear extract or recombinant protein treated with DMSO only (for maximal binding), and wells containing the extract/protein plus 20 pmoles free wild-type NF-κB oligonucleotide as a competitor or 20 pmoles free mutant NF-κB oligonucleotide as a control to demonstrate specificity. The plate was incubated for 1 hour at room temperature with gentle shaking and then washed 3 times with 200 μL 1× Wash Buffer. NF-κB p65, p50, p52, RelB, or c-Rel subunits bound to the plate were detected with 100 μL of the primary antibody (diluted 1:1000 in 1× Antibody Buffer) specific for that subunit. The plate was incubated for 1 hour at room temperature and then washed 3 times with 200 μL 1× Wash Buffer. Next, 100 μL of a HRP conjugated goat anti-rabbit antibody (diluted 1:1,000 in 1× Antibody Buffer) was added to each well. The plate was incubated for 1 hour at room temperature and then washed 4 times with 200 μL 1× Wash Buffer. 100 μL of room temperature Developing Solution was added to each well. The reaction was allowed to develop for 2-10 minutes until a medium dark blue color developed (depending on the subunit activity in the lot of extract or lot of recombinant protein used) and then the reaction was stopped with 100 μL Stop Solution yielding a yellow color. Absorbance was recorded using a Becton-Dickinson DTX 880 Multimode Detector at 450 nm with a reference wavelength subtracted at 620 nm. FIGS. 7 and 8 illustrate the effect of Example 2, DHMEQ and parthenolide on inhibiting RelA and RelB to NF-κB sites.

In addition to the compounds of Examples 1 and 2, Table 1 lists other compounds for their activities to inhibit 1) NF-κB driven expression of luciferase and GFP in HEK293 cells, 2) Il-6 and PGE2 release from RAW264 cells, and 3) binding of RelA, RelB, c-Rel, p50 and p52 ro NF-κB sites.

TABLE 1

Pharmacological activities of compounds in inhibition of NF-κB driven reporter gene expression, suppression of cytokine release and inhibition of Rel protein bindings to NF-κB sites.

| Cpd of Ex. # | 293/NFk B-luc EC50 (uM) | NF-kB/293/ GFP EC50 (uM) | RAW 264.7 IL-6 release EC50 (uM) | RAW 264.7 PGE2 release EC50 (uM) | p65 binding IC50 (uM) | p50 binding IC50 (uM) or % inhibit. at 5 uM | p52 binding IC50 (uM) or % inhibit. at 5 uM | c-Rel binding IC50 (uM) or % inhibit. at 5 uM | RelB binding IC50 (uM) or % inhibit. at 5 uM |
|---|---|---|---|---|---|---|---|---|---|
| 1 | 6.2 | 6.2 | 6.5 | 6.9 | 2.2 | 26 | 13 | 4.6 | 7.4 |
| 2 | 4.1 | 0.21 | 0.24 | 1.8 | 1.4 | 2.1 | 6 | 2.1 | 2 |
| 5 | >38 | >38 | 0.43 | 6.5 | 230 | >481 | >481 | 12% | 0% |
| 6 | 18 | 3.4 | 0.90 | 6.2 | 3.3 | 0% | 7% | 27% | 13% |
| 7 | 15 | 3.2 | 0.73 | 6.8 | 3.6 | 19% | 16% | 63% | 32% |
| 8 | 37 | 10 | 2.2 | 26.2 | N/D | 16% | 17% | 46% | 21% |
| 9 | 14 | 20 | 7.4 | 23.6 | 7.2 | 11% | 22% | 44% | 22% |
| 10 | 19 | 4.5 | <0.24 | 1.1 | 2.8 | 6% | 11% | 54% | 27% |
| 3 | 15 | 3.4 | 1.4 | N/D | 12.4 | >636 | 301 | 15% | 0% |
| 11 | 15 | 5.8 | 7.7 | N/D | 4.6 | 4% | 9% | 40% | 18% |
| 4 | >51 | 40 | >51 | N/D | 5 | 118 | 365 | 23% | 21% |
| 12 | 22 | N/D | 2.5 | N/D | 34.4 | 0% | 14% | 7% | 6% |
| 13 | 9.2 | N/D | 1.4 | N/D | 10.6 | 0% | 0% | 15% | 10% |
| 14 | 23 | N/D | 3.3 | N/D | 35.5 | 0% | 6% | 1% | 9% |
| 15 | 11 | 4.9 | 1 | N/D | 488 | 0% | 0% | 6% | 0% |
| 16 | 7.1 | 1.2 | 0.64 | N/D | 0.88 | 20 | 3.7 | 0.8 | 1.7 |
| 20 | 9.6 | 7.7 | 1.4 | N/D | 5.8 | 1% | 18% | 40% | 29% |
| 21 | 5.8 | N/D | 0.38 | N/D | 0.55 | 22 | 22 | 1.1 | 1.5 |
| 22 | >34 | N/D | >34 | N/D | 13.2 | N/D | N/D | N/D | N/D |
| 23 | >40 | >40 | 24.8 | N/D | 6.4 | N/D | N/D | N/D | N/D |

TABLE 1-continued

Pharmacological activities of compounds in inhibition of NF-κB driven reporter gene expression, suppression of cytokine release and inhibition of Rel protein bindings to NF-κB sites.

| Cpd of Ex. # | 293/NFkB-luc EC50 (uM) | NF-kB/293/GFP EC50 (uM) | RAW 264.7 IL-6 release EC50 (uM) | RAW 264.7 PGE2 release EC50 (uM) | p65 binding IC50 (uM) | p50 binding IC50 (uM) or % inhibit. at 5 uM | p52 binding IC50 (uM) or % inhibit. at 5 uM | c-Rel binding IC50 (uM) or % inhibit. at 5 uM | RelB binding IC50 (uM) or % inhibit. at 5 uM |
|---|---|---|---|---|---|---|---|---|---|
| 24 | >48 | >48 | 27.1 | N/D | 2.3 | N/D | N/D | N/D | N/D |
| 25 | 4.1 | 0.84 | 0.13 | N/D | 1.1 | 1.2 | 4.7 | 0.49 | 0.65 |
| 26 | 16 | 11 | 1.6 | N/D | 4.7 | 246 | 84 | 14 | 12 |
| 27 | 9.7 | 6.7 | 0.71 | N/D | 30 | N/D | N/D | N/D | N/D |
| 28 | 2.7 | 4.2 | 0.19 | N/D | 3 | 20 | 9.6 | 4.5 | 3.0 |
| 29 | 0.46 | 2.2 | 0.16 | N/D | 4.5 | 129 | 59 | 11 | 12 |
| 30 | 2.7 | 4.3 | 0.76 | N/D | 36 | >608 | >608 | N/D | N/D |
| 31 | 3.9 | 5.6 | 1.0 | N/D | 38 | 28 | 21 | N/D | N/D |
| 32 | 3.4 | 3.0 | 0.24 | N/D | 30 | >514 | >514 | N/D | N/D |
| 33 | 0.53 | 2.0 | 0.26 | N/D | 4.8 | >378 | >378 | N/D | N/D |
| 34 | >51 | 39 | 42 | N/D | 12 | 90 | 96 | N/D | N/D |
| 35 | 3.1 | 5.3 | 0.44 | N/D | 50 | 148 | 81 | N/D | N/D |

(N/D: not determined)

Figure 9:
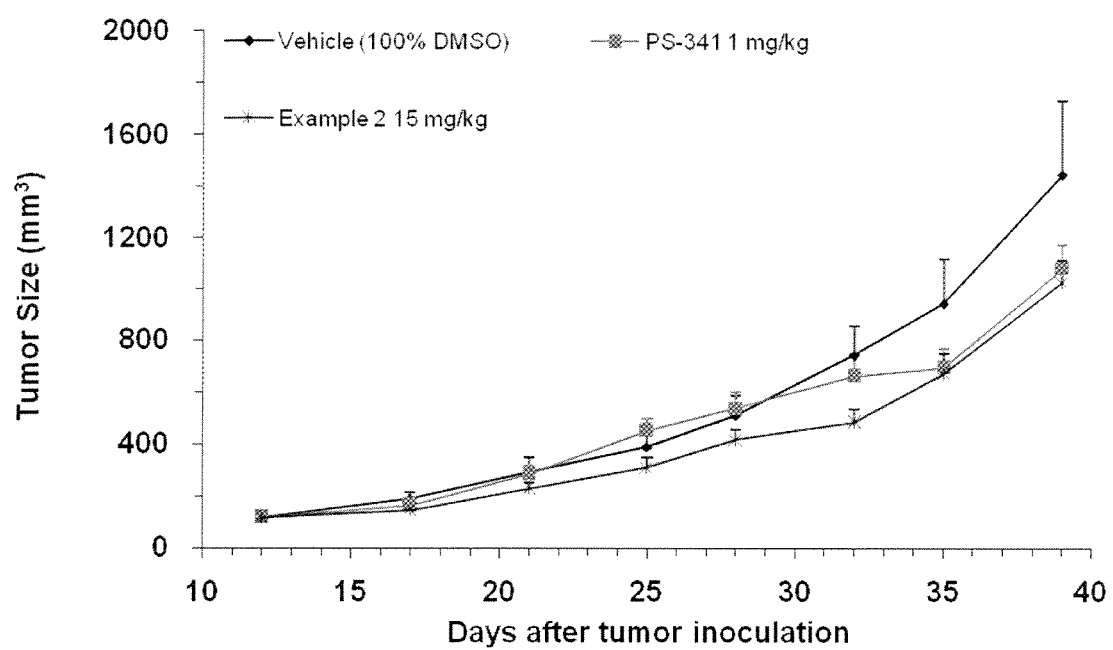
FIG. 9 shows that the compound of Example 2 reduced RPMI8226 tumor growth as bortezomib (PS-341) in xenograft mice. Neither PS-341 (1 mg/kg iv days 1, 4/week×4 weeks) nor the compound of Example 2 (15 mg/kg ip QD×21) treatment achieved statistical significant tumor growth inhibition in this study as compared to vehicle treatment (P>0.10).

In a series of in vitro experiments, the NF-κB inhibitors of the invention prevented cytokine releases and the growth of a broad spectrum of cancer cell lines. These compounds did not inhibit cytochrome P450's activities or block hERG channel. Several compounds have been assessed for efficacy studies in rodent disease models. We first sought to obtain in vivo efficacy of the compounds in multiple myeloma which has high incidence of constitutive activation of both the canonical and non-canonical pathways. In a xenograft model of human RPMI8226 multiple myeloma, the compound of Example 2 attained the same level of tumor growth reduction as PS-341 (bortezomib, Velcade®), which is approved as a first line therapy for this indication (see FIG. 9). In addition, the compound of Example 2 was better tolerated than PS-341. However, statistical analyses revealed that neither PS-341 nor Example 2 treatments achieved statistical significant tumor growth inhibition ($P>0.05$).

Inhibition of poly(ADP-ribose) polymerase-1 (PARP-1) or down-regulation of p65 (RelA) can potentiate the irradiation (IR)-induced cytotoxicity to cancer cell lines. In this study, a novel small molecule p65 (RelA) inhibitor was evaluated as a radio-sensitizing agent in wild type mouse embryonic fibroblasts (MEFs) or PARP-1$^{-/-}$ or p65$^{-/-}$ MEFs. It was found that p65$^{-/-}$ MEFs were ≥2-fold more sensitive than p65$^{+/+}$ MEFs to IR in clonogenic survival assays, thus demonstrating that NF-κB activation confers radio-resistance. Incubation with the compound of Example 2 (1.4 μM, a non-cytotoxic dose) radio-sensitized p65$^{+/+}$ MEFs (LD$_{50}$ values of 1.5 Gy for IR+ the compound of Example 2 compared with 2.3 Gy IR alone). The compound of Example 2 had no further effect on radio-sensitization of p65$^{-/-}$ MEFs, which indicates the pharmacological effect of the compound of Example 2 is mediated through p65. Similar radio-sensitizing effects were observed by using RNA interference technique to down-regulate the expression level of p65 (by >95%) in p65$^{+/+}$ MEFs but not in p65$^{-/-}$ MEFs. The compound of Example 2 was then tested in PARP-1$^{+/+}$ or PARP-1$^{+/+}$ MEFs. It was demonstrated that either the compound of Example 2 (1.4 μM) treatment or siRNA down-regulation of p65 increased radio-sensitivities of PARP-1$^{+/+}$ but not PARP-1$^{-/-}$ MEFs to IR, suggesting that PARP-1 is upstream in the activation of the NF-κB pathway. The inhibition of the NF-κB by the compound of Example 2 or p65 siRNA in MEFs was also confirmed. NF-κB-dependent luciferase expression increased by 2.5-fold after 10 Gy IR in p65$^{+/+}$ MEFs. Treatment with the compound of Example 2 or p65 siRNA reduced luciferase gene transcription significantly. Similarly, IR increased p65$^{+/+}$ MEFs nuclear extract NF-κB DNA binding activities by 2-fold, which was significantly decreased by either the compound of Example 2 incubation or p65 siRNA treatment in these cells. It was demonstrated that this p65 inhibitor can potentiate radioactivity in vitro as it was shown previously that PARP-1 inhibitors can. Further in vivo studies are required to fully explore the potential utility of the compound of Example 2 as a radio-sensitizing agent.

The objective in another study was to evaluate, in enzyme, and radioligand binding assays, the activity of the compound of Example 2. The methods employed in the study were adapted from the scientific literature to maximize reliability and reproducibility. Reference standards were run as an integral part of each assay to ensure the validity of the results obtained. Where presented, IC$_{50}$ values were determined by a non-linear, least squares regression analysis using MathIQä (ID Business Solutions Ltd., UK). Where inhibition constants (K¾) are presented, the K¾ values were calculated using the equation of Cheng and Prusoff (Cheng 1973) using the observed IC$_{50}$ of the tested compound, the concentration of radioligand employed in the assay, and the historical values for the K$^1$ of the ligand (obtained experimentally). Where presented, the Hill coefficient (n½), defining the slope of the competitive binding curve, was calculated using MathIQä. Hill coefficients significantly different than 1.0, may suggest that the binding displacement does not follow the laws of mass action with a single binding site. Where IC$_{50}$, K¾, and/or n½ data are presented without Standard Error of the Mean (SEM), data are insufficient to be quantitative. Individual responses, if requested, are presented in the appendix to this report. Results are displayed in FIG. 11 without estimated IC$_{50}$ and/or K¾ values as no inhibition was above 50%.

RNA interference screening identified p53 and ras mutations to be synthetic lethal with the canonical and non-canonical pathways of NF-κB (Barbie 2009; Meylan 2009). Inhibitors were synthesized that antagonize bindings of RelA (p65), RelB and c-rel to the NE-κB sites and thus inhibit both the canonical and non-canonical paths. One such exemplary compound, the compound of Example 2, was evaluated as a radiosensitizer in wild type and p65$^{-/-}$ mouse embryonic fibroblasts (MEFs), and as a radiosensitizing and chemotherapeutic agent in the p53 deficient and KRAS (G13D) mutant breast cancer cell line, MDA-MB-231. It was found that $p65^{-/-}$ MEFs were ≥2-fold more sensitive than $p65^{+/+}$ MEFs to irradiation (IR) in clonogenic survival assays, thus demonstrating that NF-κB activation conferred radio-resistance. Incubation with the compound of Example 2 at 1.4 µM, a non-cytotoxic concentration, radiosensitized $p65^{+/+}$ MEFs ($LD_{50}$ value of 1.5 Gy for IR+ the compound of Example 2 compared with 2.3 Gy for IR alone). The compound of Example 2 had no effect on radio-sensitization of $p65^{-/-}$ MEFs, which indicated the radiosensitizing effect of the compound of Example 2 was mediated through p65. Similar radiosensitizing effects were observed by using RNA interference technique to down-regulate the expression level of p65 by >95% in $p65^{+/+}$ MEFs but not in $p65^{-/-}$ MEFs. The inhibition of the NF-κB by the compound of Example 2 or p65 siRNA in MEFs was also confirmed. NF-κB-dependent luciferase expression increased by 2.5 fold after 10 Gy IR in $p65^{+/+}$ MEFs. Treatment with the compound of Example 2 or p65 siRNA significantly reduced luciferase expression. Similarly, IR increased $p65^{+/+}$ MEFs nuclear extract NF-κB DNA binding activities by 2 fold, which was significantly decreased by either the compound of Example 2 incubation or p65 siRNA treatment in these cells.

The compound of Example 2 was also studied in MDA-MB-231 breast cancer cells with constitutive NF-κB activation. First, the compound of Example 2 was tested as a single agent on the growth of the breast cancer cells. Significant cytotoxic effect to the compound of Example 2 was observed with an $LD_{50}$ value of 0.4 µM to the MDA-MB-231 cells. Then the synergistic effect of the compound of Example 2 was tested with irradiation in these cells. Incubation with 0.2 µM the compound of Example 2 was observed to significantly enhance radiation effect by 1.5 fold ($LD_{50}$ value of 1.66 Gy IR for IR+ the compound of Example 2 compared with 2.55 Gy for IR alone). These described studies demonstrate that a Rel inhibitor of NF-κB can potentiate radioactivity through blocking the canonical pathway. It can also selectively kill tumor cells with p53 and KRAS mutations, perhaps through blocking both the canonical and non-canonical pathways.

Figure 10:
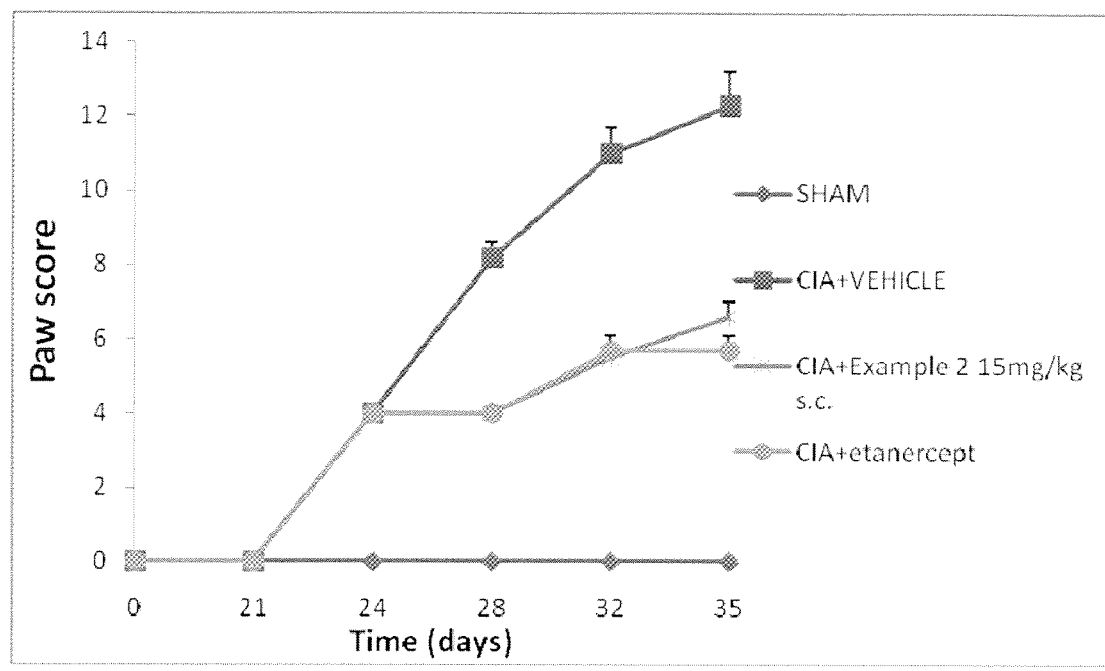
FIG. 10 shows that the compound of Example 2 exhibited anti-inflammatory efficacy as etanercept in a mouse model of collagen-induced rheumatoid arthritis (CIA). Both the compound of Example 2 (15 mg/kg s.c. qd 21-35) and etanercept (50 ug/mouse ip qd 21-35) treatment group achieved statistal significant anti-inflammation effects (P<0.05 compared to vehicle treated group).

A recent genome-wide association study of rheumatoid arthritis has identified the REL locus, encoding c-Rel, as a newly defined risk factor for the disease (Gregersen 2009). c-Rel is a member of the NF-κB family of transcription factors that mediate both the canonical and non-canonical pathways of NF-κB. Mice with a genetic deletion of c-Rel are resistant to collagen-induced arthritis. Low molecular weight inhibitors have been synthesized that block the binding of c-Rel, RelA and RelB to the NF-κB sites. The anti-inflammatory activities of the compound of Example 2, a dual inhibitor of both the canonical and non-canonical pathways of NF-κB, in a mouse model of collagen-induced arthritis. The effect of the compound of Example 2 with etanercept, the TNFα blocker, was compared in a mouse model of rheumatoid arthritis. Male DBA mice developed arthritis by injecting bovine CII collagen in tails at day 1 and day 21. Groups of animals (n=10) were treated with 1) sham operation, 2) vehicle (DMSO), 3) etanercept (50 µg/mouse, i.p daily d21-d35), 4) compound of Example 2 (15 mg/kg, s.c. daily d21-d35), 5) the compound of Example 2 (15 mg/kg, i.p. daily d21-d35), 6) the compound of Example 2 (50 mg/kg, i.p. daily d21-d35). The compound of Example 2 treatment significantly reduced mouse hind paw erythema and swelling, comparable to etanercept treatment, as assessed by the arthritis index score (FIG. 10). Both etanercept and the compound of Example 2 reduced paw edema (P<0.01 vs vehicle group). No significant difference in weight loss was observed in mice in all experimental groups. The histological evaluation of joints at day 35 revealed a significant reduction of inflammation in mice treated with the compound of Example 2 or etanercept. A measurement of myeloperoxidase activities showed a concomitant reduction of the granulocyte lysozome specific enzyme due to the compound of Example 2 or etanercept treatment. In conclusion, we have demonstrated that a Rel inhibitor of NF-κB can protect mice from the development of inflammatory arthritis The anti-inflammatory activities of the compound of Example 2 are comparable to those of etanercept in the mouse rheumatoid arthritis model. The efficacy of the compound of Example 2 is achieved at doses well tolerated by the mice.

The NF-κB inhibitors of the invention are being tested as anti-inflammatory agents in animal models of colitis, as a radiosensitizer for irradiation treatment of solid tumors, as chemotherapeutic agents either alone or in combination with various approved cancer drugs. Both dual inhibitors for the canonical and non-canonical paths and sole inhibitors for the canonical path are being characterized.

Without further description, it is believed that one of ordinary skill in the art can, using the preceding description and the illustrative examples, make and utilize the compounds of the present invention and practice the claimed methods. While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. All patents, patent applications and other references cited throughout this application are herein incorporated by reference in their entirety.

REFERENCES

Aggarwal B B, Shishodia S, Sandur S K, Pandey M K, Sethi G (2006) Inflammation and cancer: how hot is the link? *Biochem Pharmacol* 72(11): 1605-1621;

Arcaroli J, Silva E, Maloney J P, He Q, Svetkauskaite D, Murphy J R, Abraham E (2006) Variant IRAK-1 haplotype is associated with increased nuclear factor-kappaB activation and worse outcomes in sepsis. *Am J Respir Crit Care Med* 173(12): 1335-1341;

Argyropoulos C, Mouzaki A (2006) Immunosuppressive drugs in HIV disease. *Curr Top Med Chem* 6(16): 1769-1789;

Ariga A, Namekawa J-i, Matsumoto N, Inoue J-i, Umezawa K (2002) Inhibition of tumor necrosis factor0alpha-induced nuclear translocation and activation of NF-kappaB by dehydroxymethylepoxyquinomicin. J. Biol. Chem. 277(27): 24625-24630;

Atreya I, Atreya R, Neurath M F (2008) NF-kappaB in inflammatory bowel disease. *J Intern Med* 263(6): 591-596;

Baba M (2006) Recent status of HIV-1 gene expression inhibitors. *Antiviral Res* 71(2-3): 301-306;

Barbie D A, Tamayo P, Boehm J S et al. (2009) Systematic RNA interference reveals that oncogenic KRAS-driven cancers require TBK1. *Nature* 462(7269): 108-112;

Barnes P J (1997) Nuclear factor-kappa B. *Int J Biochem Cell Biol* 29(6): 867-870;

Bosisio D, Marazzi I, Agresti A, Shimizu N, Bianchi M E, Natoli G (2006) A hyper-dynamic equilibrium between promoter-bound and nucleoplasmic dimers controls NF-kappaB-dependent gene activity. *Embo J* 25(4): 798-810;

Bouma G, Strober W (2003) The immunological and genetic basis of inflammatory bowel disease. *Nat Rev Immunol* 3(7): 521-533;

Burstein E, Duckett C S (2003) Dying for NF-kappaB? Control of cell death by transcriptional regulation of the apoptotic machinery. *Curr Opin Cell Biol* 15(6): 732-737;

Calzado M A, Bacher S, Schmitz M L (2007) NF-kappaB inhibitors for the treatment of inflammatory diseases and cancer. *Curr Med Chem* 14(3): 367-376;

Chaicharoenpong C, Kato K, Umezawa K (2002) Synthesis and structure-activity relationship of dehydroxymethylepoxyquinomicin analogues as inhibitors of NF-kappaB functions. *Bioorg Med Chem* 10(12): 3933-3999;

Cheng Y, Prusoff W H (1973) Relationship between the inhibition constant (K1) and the concentration of inhibitor which causes 50 percent inhibition (ISO) of an enzymatic reaction *Biochem. Pharmacol.* 22:3099-3108;

Dejardin E (2006) The alternative NF-kappaB pathway from biochemistry to biology: pitfalls and promises for future drug development. *Biochem. Pharmacol.* 72:1161-1179;

Flory E, Kunz M, Scheller C, Jassoy C, Stauber R, Rapp U R, Ludwig S (2000) Influenza virus-induced NF-kappaB-dependent gene expression is mediated by overexpression of viral proteins and involves oxidative radicals and activation of IkappaB kinase. *J Biol Chem* 275(12): 8307-8314;

Giri R K, Rajagopal V, Shahi S, Zlokovic B V, Kalra V K (2005) Mechanism of amyloid peptide induced CCR5 expression in monocytes and its inhibition by siRNA for Egr-1. *Am J Physiol Cell Physiol* 289(2): C264-276;

Goldring S R, Jasty M, Roelke M S, Rourke C M, Bringhurst F R, Harris W H (1986) Formation of a synovial-like membrane at the bone-cement interface. Its role in bone resorption and implant loosening after total hip replacement. *Arthritis Rheum* 29(7): 836-842;

Greten F R, Karin M (2004) The IKK/NF-kappaB activation pathway-a target for prevention and treatment of cancer. *Cancer Lett* 206(2): 193-199;

Gregersen P K, Amos C L, Lee At et al. (2009) REL, encoding a member of the NF-kappaB family of transcription factors, is a newly defined risk locus for rheumatoid arthritis. *Nat Genet* 41(7): 820-823;

Hacker H, Karin M (2006) Regulation and function of IKK and IKK-related kinases. *Sci STKE* 2006(357): re13;

Harris W H (1995) The problem is osteolysis. *Clin Orthop Relat Res*(311): 46-53;

Hayden M S, Ghosh S (2004) Signaling to NF-kappaB. *Genes Dev* 18(18): 2195-2224;

Hayden M S, West A P, Ghosh S (2006a) NF-kappaB and the immune response. *Oncogene* 25(51): 6758-6780;

Hayden M S, West A P, Ghosh S (2006b) SnapShot: NF-kappaB Signaling Pathways. *Cell* 127(6): 1286-1287;

Helbig G, Christopherson K W, 2nd, Bhat-Nakshatri P, Kumar S, Kishimoto H, Miller K D, Broxmeyer H E, Nakshatri H (2003) NF-kappaB promotes breast cancer cell migration and metastasis by inducing the expression of the chemokine receptor CXCR4. *J Biol Chem* 278(24): 21631-21638;

Iordanskiy S, Iordanskaya T, Quivy V, Van Lint C, Bukrinsky M (2002) B-oligomer of pertussis toxin inhibits HIV-1 LTR-driven transcription through suppression of NF-kappaB p65 subunit activity. *Virology* 302(1): 195-206;

Israel A (2000) The IKK complex: an integrator of all signals that activate NF-kappaB? *Trends Cell Biol* 10(4): 129-133;

Jung M, Zhang Y, Lee S, Dritschilo A (1995) Correction of radiation sensitivity in ataxia telangiectasia cells by a truncated I kappa B-alpha. *Science* 268(5217): 1619-1621;

Karin M (1999) How NF-kappaB is activated: the role of the IkappaB kinase (IKK) complex. *Oncogene* 18(49): 6867-6874;

Karin M (2006) Nuclear factor-kappaB in cancer development and progression. *Nature* 441(7092): 431-436;

Ketas T J, Kuhmann S E, Palmer A, Zurita J, He W, Ahuja S K, Klasse P J, Moore J P (2007) Cell surface expression of CCR5 and other host factors influence the inhibition of HIV-1 infection of human lymphocytes by CCR5 ligands. *Virology* 364(2):281-90;

Lawrence R C, Helmick C G, Arnett F C, Deyo R A, Felson D T, Giannini E H, Heyse S P, Hirsch R, Hochberg M C, Hunder G G, Liang M H, Pillemer S R, Steen V D, Wolfe F (1998) Estimates of the prevalence of arthritis and selected musculoskeletal disorders in the United States. *Arthritis Rheum* 41(5): 778-799;

Liao F, Andalibi A, Qiao J H, Allayee H, Fogelman A M, Lusis A J (1994) Genetic evidence for a common pathway mediating oxidative stress, inflammatory gene induction, and aortic fatty streak formation in mice. *J Clin Invest* 94(2): 877-884;

Liu R, Zhao X, Gurney T A, Landau N R (1998) Functional analysis of the proximal CCR5 promoter. *AIDS Res Hum Retroviruses* 14(17): 1509-1519;

Maruyama I, Shigeta K, Miyahara H, Nakajima T, Shin H, Ide S, Kitajima I (1997) Thrombin activates NF-kappa B through thrombin receptor and results in proliferation of vascular smooth muscle cells: role of thrombin in atherosclerosis and restenosis. *Ann N Y Acad Sci* 811: 429-436;

Meylan E, Dooley A L, Feldser D M et al. (2009) Requirement for NF-kappaB signalling in a mouse model of lung adenocarcinoma. *Nature* 462(7269):104-107;

Mukerjee R, Sawaya B E, Khalili K, Amini S (2006) Association of p65 and C/EBPbeta with HIV-1 LTR modulates transcription of the viral promoter. *J Cell Biochem* 100(5): 1210-6;

Natoli G, Saccani S, Bosisio D, Marazzi I (2005) Interactions of NF-kappaB with chromatin: the art of being at the right place at the right time. *Nat Immunol* 6(5): 439-445;

Neurath M F, Fuss I, Schurmann G, Pettersson S, Arnold K, Muller-Lobeck H. Strober W, Herfarth C, Buschenfelde K H (1998) Cytokine gene transcription by NF-kappa B family members in patients with inflammatory bowel disease. *Ann N Y Acad Sci* 859: 149-159;

Niu J, Azfer A, Kolattukudy P E (2008) Protection against lipopolysaccharide-induced myocardial dysfunction in mice by cardiac-specific expression of soluble Fas. *J Mol Cell Cardiol* 44(1): 160-169;

Pahl H L, Baeuerle P A (1995) Expression of influenza virus hemagglutinin activates transcription factor NF-kappa B. *J Virol* 69(3): 1480-1484;

Palmieri C, Trimboli F, Puca A, Fiume G, Scala G, Quinto I (2004) Inhibition of HIV-1 replication in primary human monocytes by the IkappaB-alphaS32/36A repressor of NF-kappaB. *Retrovirology* 1(1): 45;

Pihlstrom B L, Michalowicz B S, Johnson N W (2005) Periodontal diseases. *Lancet* 366(9499): 1809-1820;

Platt E J, Wehrly K, Kuhmann S E, Chesebro B, Kabat D (1998) Effects of CCR5 and CD4 cell surface concentrations on infections by macrophagetropic isolates of human immunodeficiency virus type 1. *J Virol* 72(4): 2855-2864;

Reeves J D, Gallo S A, Ahmad N, Miamidian J L, Harvey P E, Sharron M, Pohlmann S, Sfakianos J N, Derdeyn C A, Blumenthal R, Hunter E, Doms R W (2002) Sensitivity of HIV-1 to entry inhibitors correlates with envelope/coreceptor affinity, receptor density, and fusion kinetics. *Proc Natl Acad Sci USA* 99(25): 16249-16254;

Rizzi C, Alfano M, Bugatti A, Camozzi M, Poli G, Rusnati M (2004) Inhibition of intra- and extra-cellular Tat function and HIV expression by pertussis toxin B-oligomer. *Eur J Immunol* 34(2): 530-536;

Saccani S, Marazzi I, Beg A A, Natoli G (2004) Degradation of promoter-bound p65/RelA is essential for the prompt termination of the nuclear factor kappaB response. *J Exp Med* 200(1): 107-113;

Scheidereit C (2006) IkappaB kinase complexes: gateways to NF-kappaB activation and transcription. *Oncogene* 25(51): 6685-6705;

Sui Z, Sniderhan L F, Fan S, Kazmierczak K, Reisinger E, Kovacs A D, Potash M J, Dewhurst S, Gelbard H A, Maggirwar S B (2006) Human immunodeficiency virus-encoded Tat activates glycogen synthase kinase-3beta to antagonize nuclear factor-kappaB survival pathway in neurons. *Eur J Neurosci* 23(10): 2623-2634;

Takeuich T, Umezawa K, To-E S, Matsumoto N, Sawa T, Yoshioka T, Agata N, Hirano S-i, Isshiki K (2003) Salicylamide deratives. U.S. Pat. No. 6,566,394 B1;

Tergaonkar V (2006) NFkappaB pathway: a good signaling paradigm and therapeutic target. *Int J Biochem Cell Biol* 38(10): 1647-1653;

Tilg H, Moschen A R, Kaser A, Pines A, Dotan I (2008) Gut, inflammation and osteoporosis: basic and clinical concepts. *Gut* 57(5): 684-694;

Suzuki Y, Sugiyama C, Ohno O, Umezawa K (2004) Preparation and biological activities of optically active dehydroxymethylepoxyquinomicin, a novel NF-κB inhibitor. *Tetrahedron* 60:7061-7066;

Umezawa K (2006) Inhibition of tumor growth by NF-kappaB inhibitors. *Cancer Sci* 97(10):990-995;

Williams S A, Chen L F, Kwon H, Ruiz-Jarabo C M, Verdin E, Greene W C (2006) NF-kappaB p50 promotes HIV latency through HDAC recruitment and repression of transcriptional initiation. *Embo J* 25(1): 139-149;

Williams S A, Kwon H, Chen L F, Greene W C (2007) Sustained Induction of NF-{kappa} B Is Required for Efficient Expression of Latent HIV-1. *J Virol* 81(11):6043-56;

Wirtz S, Neurath M F (2007) Mouse models of inflammatory bowel disease. *Adv Drug Deliv Rev* 59(11): 1073-1083;

Yamamoto M, Horie R, Takeiri M, Kozawa I, Umezawa K (2008) Inactivation of NF-kappaB components by covalent binding of (−)-dehydroxymethylepoxyquinomicin to specific cysteine residues. *J. Med Chem* 51(8):5780-5788;

The invention claimed is:

1. A compound of formula (1) or formula (2):

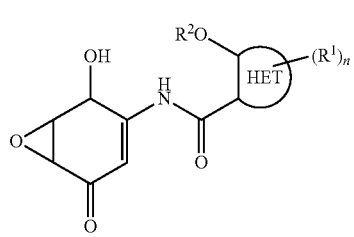

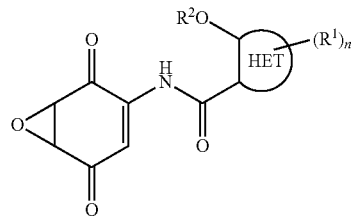

or a pharmaceutical salt thereof,
wherein:
HET is a saturated or unsaturated mono- or multi-ring carbocycle in which one or more of the ring carbon atoms is replaced by N, S, P or O;
each $R^1$ is independently hydrogen; $CF_3$; phenyl optionally substituted with cyano, halo, nitro, hydroxyl, (C1-C6) alkyl, (C1-C6)alkyl-OH, (C1-C6)alkoxy, $COR^3$, $NR^4R^5$ or NHCO(C1-C6) alkyl; cyano; halo; nitro; hydroxyl; (C1-C6)alkyl; (C1-C6)alkyl-OH; (C1-C6)alkoxy; (C1-C6)thioalkoxy; phenoxy; $COR^3$; $NR^4R^5$; NHCO(C1-C6) alkyl; $SO_2$(C1-C6) alkyl; or $SO_2NR^4R^5$;
$R^2$ is H, $R^6$, $COR^6$, $CONHR^6$, $COOR^6$, $CH_2OCOR^6$, $P(O)(OH)_2$, $P(O)(O(C1-C6)alkyl)_2$, $P(O)(OCH_2OCO(C1-C6)alkyl)_2$, $P(O)(OH)(OCH_2OCO(C1-C6)alkyl)$, $P(O)(OH)(O(C1-C6)alkyl)$, $P(O)(OH)(C1-C6)alkyl$, glycosyl or an inorganic salt of $P(O)(OH)_2$, $P(O)(O(C1-C6)alkyl)_2$, $P(O)(OCH_2OCO(C1-C6)alkyl)_2$, $P(O)(OH)(OCH_2OCO(C1-C6)alkyl)$, $P(O)(OH)(OC1-C6)alkyl$ or $P(O)(OH)(C1-C6)alkyl$;
$R^6$ is C1-C6 alkyl, trifluoromethyl, (C3-C6)cycloalkyl, cyclohexylmethyl or phenyl, wherein the phenyl is substituted with 0 to 4 groups selected from the group consisting of fluorine, chlorine, bromine, hydroxyl, trifluoromethyl, (C1-C4)alkyl, (C1-C4)alkoxy and phenylmethyl, wherein the phenylmethyl is substituted on the phenyl ring with 0-4 groups selected from the group consisting of fluorine, chlorine, bromine, hydroxyl, trifluoromethyl, (C1-C4)alkyl, (C1-C4) alkoxy, 2-pyridinyl, 3-pyridinyl, 4-pyridinyl, 2-pyrimidinyl, 4-pyrimidinyl, and 5-pyrimidinyl;
$R^3$ is independently hydroxyl, (C1-C6)alkoxy, phenoxy or $-NR^4R^5$;
each $R^4$ and $R^5$ are independently hydrogen, (C1-C6)alkyl or (C3-C6)cycloalkyl; and
n is 0-3,
wherein on HET, there exists an ortho relationship between the $OR^2$ group and the amide moiety.

2. The compound of claim 1, wherein $R^2$ is H.

3. The compound of claim 1, wherein HET is pyridyl and n is 0.

4. The compound of claim 1, having the structure of formula (3):

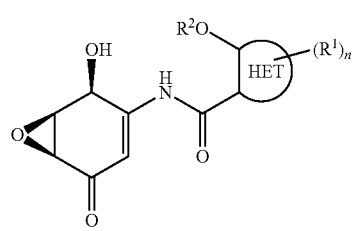

or a pharmaceutically acceptable salt thereof.

5. The compound of claim 4, wherein $R^2$ is H.

6. A pharmaceutical composition comprising a compound of formula (1) or formula (2) according to claim 1 or a pharmaceutically acceptable salt thereof in combination with a pharmaceutically effective diluent or carrier.

7. A pharmaceutical composition comprising a compound of formula (3) according to claim 4 or a pharmaceutically acceptable salt thereof in combination with a pharmaceutically effective diluent or carrier.

8. The compound of claim 2, wherein HET is pyridyl and n is 0.

9. The compound of claim 1 or pharmaceutical salt thereof, which is selected from the group consisting of:
- (±)-2-hydroxy-N-(2-hydroxy-5-oxo-7-oxa-bicyclo[4.1.0]hept-3-en-3-yl)nicotinamide;
- (±)-2-hydroxy-N-(2-hydroxy-5-oxo-7-oxa-bicyclo[4.1.0]hept-3-en-3-yl)quinoline-3-carboxamide;
- (±)-3-hydroxy-N-(2-hydroxy-5-oxo-7-oxa-bicyclo[4.1.0]hept-3-en-3-yl)picolinamide;
- (±)-4-hydroxy-N-(2-hydroxy-5-oxo-7-oxa-bicyclo[4.1.0]hept-3-en-3-yl)-nicotinamide;
- (±)-6-chloro-4-hydroxy-quinoline-3-carboxylic acid-(2-hydroxy-5-oxo-7-oxa-bicyclo[4.1.0]hept-3-en-3-yl)-amide;
- (±)-4-hydroxy-8-trifluoromethyl-quinoline-3-carboxylic acid-(2-hydroxy-5-oxo-7-oxa-bicyclo[4.1.0]hept-3-en-3-yl)-amide;
- (±)-5-chloro-2-hydroxy-N-(2-hydroxy-5-oxo-7-oxa-bicyclo[4.1.0]hept-3-en-3-yl)-nicotinamide;
- (±)-4-hydroxy-2-phenylpyrimidine-5-carboxylic acid (2-hydroxy-5-oxo-7-oxa-bicyclo[4.1.0]hept-3-en-3-yl)-amide;
- (±)-3-hydroxy-quinoxaline-2-carboxylic acid (2-hydroxy-5-oxo-7-oxa-bicyclo[4.1.0]hept-3-en-3-yl)-amide;
- (±)-2-hydroxy-N-(2-hydroxy-5-oxo-7-oxa-bicyclo[4.1.0]hept-3-en-3-yl)-6-methyl-nicotinamide;
- (±)-4-hydroxy-2-piperidin-1-yl-pyrimidine-5-carboxylic acid (2-hydroxy-5-oxo-7-oxa-bicyclo[4.1.0]hept-3-en-3-yl)-amide;
- (±)-3-hydroxy-N-(2-hydroxy-5-oxo-7-oxa-bicyclo[4.1.0]hept-3-en-3-yl)picolinamide, mesylate;
- (±)-3-hydroxy-N-(2-hydroxy-5-oxo-7-oxa-bicyclo[4.1.0]hept-3-en-3-yl)picolinamide trifluoroacetate;
- (±)-3-hydroxy-N-(2-hydroxy-5-oxo-7-oxa-bicyclo[4.1.0]hept-3-en-3-yl)picolinamide tosylate;
- (±)-3-hydroxy-quinoline-2-carboxylic acid-(2-hydroxy-5-oxo-7-oxa-bicyclo[4.1.0]hept-3-en-3-yl)-amide;
- (±)-N-(2-hydroxy-5-oxo-7-oxa-bicyclo[4.1.0]hept-3-en-3-yl)-2-methoxy-nicotinamide;
- (±)-3-hydroxy-quinoline-2-carboxylic acid-(2-hydroxy-5-oxo-7-oxa-bicyclo[4.1.0]hept-3-en-3-yl)-amide mesylate;
- (±)-3-hydroxy-quinoline-2-carboxylic acid-(2-hydroxy-5-oxo-7-oxa-bicyclo[4.1.0]hept-3-en-3-yl)-amide trifluoroacetate;
- (±)-3-hydroxy-quinoline-2-carboxylic acid-(2-hydroxy-5-oxo-7-oxa-bicyclo[4.1.0]hept-3-en-3-yl)-amide tosylate;
- (±)-3-methoxy-pyridine-2-carboxylic acid (2-hydroxy-5-oxo-7-oxa-bicyclo[4.1.0]hept-3-en-3-yl)-amide;
- (±)-N-(2-hydroxy-5-oxo-7-oxa-bicyclo[4.1.0]hept-3-en-3-yl)-2-methoxy-nicotinamide trifluoroacetate;
- (±)-3-methoxy-pyridine-2-carboxylic acid (2-hydroxy-5-oxo-7-oxa-bicyclo[4.1.0]hept-3-en-3-yl)-amide trifluoroacetate;
- (±)-2-hydroxy-N-(2-hydroxy-5-oxo-7-oxa-bicyclo[4.1.0]hept-3-en-3-yl)-6-trifluoromethyl-nicotinamide;
- (±)-4-hydroxy-2-methyl-pyrimidine-5-carboxylic acid (2-hydroxy-5-oxo-7-oxa-bicyclo[4.1.0]hept-3-en-3-yl)-amide;
- (±)-2-methoxy-quinoline-3-carboxylic acid (2-hydroxy-5-oxo-7-oxa-bicyclo[4.1.0]hept-3-en-3-yl)-amide;
- (±)-3-methoxy-pyrazine-2-carboxylic acid (2-hydroxy-5-oxo-7-oxa-bicyclo[4.1.0]hept-3-en-3-yl)-amide;
- (±)-1-chloro-4-hydroxy-isoquinoline-3-carboxylic acid (2-hydroxy-5-oxo-7-oxa-bicyclo[4.1.0]hept-3-en-3-yl)-amide;
- (±)-N-(2,5-dioxo-7-oxa-bicyclo[4.1.0]hept-3-en-3-yl)-2-hydroxyquinoline-3-carboxamide;
- (±)-N-(2-hydroxy-5-oxo-7-oxa-bicyclo[4.1.0]hept-3-en-3-yl)-8-methoxyquinoline-7-carboxamide;
- (±)-N-(2,5-Dioxo-7-oxa-bicyclo[4.1.0]hept-3-en-3-yl)-2-methoxy-nicotinamide (±)-N-(2-hydroxy-5-oxo-7-oxa-bicyclo[4.1.0]hept-3-en-3-yl)-3-methoxyquinoline-2-carboxamide;
- (±)-N-(2,5-dioxo-7-oxa-bicyclo[4.1.0]hept-3-en-3-yl)-8-methoxyquinoline-7-carboxamide;
- (±)-N-(2-hydroxy-5-oxo-7-oxa-bicyclo[4.1.0]hept-3-en-3-yl)-8-methoxyquinoline-7-carboxamide trifluoroacetate;
- (±)-N-(2,5-dioxo-7-oxa-bicyclo[4.1.0]hept-3-en-3-yl)-3-hydroxyisonicotinamide (±)- N-(2,5-dioxo-7-oxa-bicyclo[4.1.0]hept-3-en-3-yl)-2-methoxyquinoline-3-carboxamide;
- (±)-2-hydroxy-N-(2-hydroxy-5-oxo-7-oxa-bicyclo[4.1.0]hept-3-en-3-yl)-6-methoxyquinoline-3-carboxamide;
- (±)-6-hydroxy-N-(2-hydroxy-5-oxo-7-oxa-bicyclo[4.1.0]hept-3-en-3-yl)benzo[d]oxazole-5-carboxamide;
- (±)-6-hydroxy-N-(2-hydroxy-5-oxo-7-oxa-bicyclo[4.1.0]hept-3-en-3-yl)benzo[d]thiazole-5-carboxamide;
- (±)-3-hydroxy-N-(2-hydroxy-5-oxo-7-oxa-bicyclo[4.1.0]hept-3-en-3-yl)piperidine-2-carboxamide;
- (±)-3-hydroxy-N-(2-hydroxy-5-oxo-7-oxa-bicyclo[4.1.0]hept-3-en-3-yl)pyrazine-2-carboxamide;
- (±)-5-hydroxy-N-(2-hydroxy-5-oxo-7-oxa-bicyclo [4.1.0]hept-3-en-3-yl)pyrimidine-4-carboxamide;
- (±)-2-hydroxy-N-(2-hydroxy-5-oxo-7-oxa-bicyclo[4.1.0]hept-3-en-3; -yl)-1,8-naphthyridine-3-carboxamide;
- (±)-7-hydroxy-N-(2-hydroxy-5-oxo-7-oxa-bicyclo[4.1.0]hept-3-en-3-yl)pyrido[2,3-d]pyrimidine-6-carboxamide;
- (±)-4-hydroxy-N-(2-hydroxy-5-oxo-7-oxa-bicyclo[4.1.0]hept-3-en-3-yl)pyridazine-3-carboxamide;
- (±)-4-hydroxy-N-(2-hydroxy-5-oxo-7-oxa-bicyclo[4.1.0]hept-3-en-3-yl)-1H-pyrazole-3-carboxamide;
- 4-hydroxy-N-(2-hydroxy-5-oxo-7-oxa-bicyclo[4.1.0]hept-3-en-3-yl)furan-3-carboxamide;
- (±)-4-hydroxy-N-(2-hydroxy-5-oxo-7-oxa-bicyclo[4.1.0]hept-3-en-3-yl)thiophene-3-carboxamide;
- (±)-3-hydroxy-N-(2-hydroxy-5-oxo-7-oxa-bicyclo[4.1.0]hept-3-en-3-yl)isothiazole-4-carboxamide;
- (±)-3-hydroxy-N-(2-hydroxy-5-oxo-7-oxa-bicyclo[4.1.0]hept-3-en-3-yl)isoxazole-4-carboxamide;
- (±)-6-hydroxy-N-(2-hydroxy-5-oxo-7-oxa-bicyclo[4.1.0]hept-3-en-3-yl)-1H-indole-5-carboxamide;
- (±)-6-hydroxy-N-(2-hydroxy-5-oxo-7-oxa-bicyclo[4.1.0]hept-3 -en-3 -yl)-1H-benzo[d]imidazole-5-carboxamide; and
- (±)-2-hydroxy-N-(2-hydroxy-5-oxo-7-oxa-bicyclo[4.1.0]hept-3-en-3-yl)morpholine-3-carboxamide.

* * * * *